US006844161B2

(12) United States Patent
Siani et al.

(10) Patent No.: US 6,844,161 B2
(45) Date of Patent: Jan. 18, 2005

(54) MODULAR PROTEIN LIBRARIES AND METHODS OF PREPARATION

(75) Inventors: Michael A. Siani, San Francisco, CA (US); Jill Wilken, San Francisco, CA (US); Reyna Simon, Los Gatos, CA (US); Stephen B. H. Kent, San Francisco, CA (US)

(73) Assignee: Gryphon Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 09/144,838

(22) Filed: Aug. 31, 1998

(65) Prior Publication Data

US 2002/0051996 A1 May 2, 2002

Related U.S. Application Data

(60) Provisional application No. 60/057,620, filed on Sep. 4, 1997.

(51) Int. Cl.[7] .......................... C12Q 1/00; G01N 33/53; C07K 14/00

(52) U.S. Cl. .................... 435/7.1; 435/4; 435/DIG. 46; 530/324; 530/350

(58) Field of Search ...................... 435/4, 7.1, DIG. 46; 530/324, 350

(56) References Cited

U.S. PATENT DOCUMENTS

| 5,508,261 A | 4/1996 | Moyle et al. |
| 6,184,344 B1 * | 2/2001 | Kent et al. .................. 530/323 |
| 6,326,468 B1 * | 12/2001 | Kent et al. .................. 530/333 |

FOREIGN PATENT DOCUMENTS

| EP | 0156588 | 10/1985 |
| EP | 0503683 | 9/1992 |
| WO | WO 92/22368 | 12/1992 |
| WO | WO 93/06844 | 4/1993 |
| WO | WO 93/20098 | 10/1993 |
| WO | WO 94/01102 | 1/1994 |
| WO | WO 95/00846 | 1/1995 |
| WO | WO 95/04543 | 2/1995 |
| WO | WO 95/34641 | 12/1995 |
| WO | WO 96/34878 | 11/1996 |
| WO | WO 97/30161 | 8/1997 |
| WO | WO 98/28434 | 7/1998 |
| WO | WO 98/56807 | 12/1998 |

OTHER PUBLICATIONS

Campbell, J.J. et al., "Chemokines and the Arrest of Lymphocytes Rolling Under Flow Conditions," *Science* (1998) 279:381–384.

Canne, L.E. et al., "Solid Phase Protein Synthesis by Chemical Ligation of Unprotected Peptide Segments in Aqueous Solution," The 1997 American Peptide Symposium, Nashville, Tennessee, Jun. 14–19, 1997.

Cohen, J., "Exploiting the HIV–Chemokine Nexus," *Science* (1997) 275:1261–1264.

Moore, P.S. et al., "Molecular Mimicry of Human Cytokine andCytokine Response Pathway Genes by KSHV," *Science* (1996) 274:1739–1744.

Nord, K. et al., "Binding Proteins Selected from Combinatorial Libraries of an α–Helical Bacterial Receptor Domain," *Nature Biotechnology* (1997) 15:772–777.

Siani, M.A. et al., "Rapid Modular Synthesis of Chemokines and Analogues," Poster, pp. 1–13, International Business Communications 3rd Annual International Conference on Chemokines, San Francisco, CA, USA, Sep. 30 –Oct. 1st, 1996.

Wilken, J. and Kent, S.B.H., "Chemical Protein Synthesis," *Curr. Opinions Biotechnol.* (1998) 9:412–426.

Beall et al., "Site–directed mutagenesis of monocyte chemoattractant protein–1 identifies two regions of the polypeptide essential for biological activity," *Biochemistry* (1996) 313:633–640.

Ben–Efraim et al., "Secondary structure and membrane localization of synthetic segments and a truncated from of the IsK (minK) protein," *Biochemistry* (1994) 33:6966–6973.

Bleul et al. , " The lymphocte chemoattractant SDF–1 is a ligand for LESTR/fusion and blocks HIV–1 entry," *Nature* (1996) 382–829.

Boshoff et al., "Angiogenic and HIV–inhibitory functions of KSHV–encoded chemokines," *Science* (1997) 278:290–294.

Brenner et al., "Encoded combinatorial chemistry," *Proc. Natl. Acad. Sci. U.S.A.* (1992) 89:5381–5383.

Bunin et al., "The combinatorial synthesis and chemical and biological evaluation of a 1,4,–benzodiazepine library," *Proc. Natl. Acad. Sci. USA* (1993) 91:4708–4712.

Canne et al., "Total chemical synthesis of a unique transcription factor–related protein—CMYC–MAX," *J. Am. Chem. Soc* (1995) 117:2998–3007.

Canne et al., "A general method for the synthesis of thioester resin linkers for use in the solid phase synthesis of peptide–alpha–thioacids," *Tetrahedron Lett.* (1995) 36:1217–1220.

Carrasco et al., "Direct monitoring of organic reactions on polymeric supports," *Tetrahedron Letters* (1997) 38:6331–6334.

(List continued on next page.)

*Primary Examiner*—Bennett Celsa
(74) *Attorney, Agent, or Firm*—Jeffrey I. Auerbach; Liniak, Berenato & White

(57) ABSTRACT

Novel proteins and protein libraries are disclosed. The proteins possess one or more functional protein modules from different parent protein molecules. The proteins and protein libraries are exemplified by the preparation of crossover chemokines that contain various combinations of peptide segments derived from RANTES, SDS-1 and vMIP-I and to vMIP-II. The proteins and libraries are extremely pure and can be provided in non-limiting high yields suitable for diagnostic and high-throughput screening assays.

35 Claims, 4 Drawing Sheets

OTHER PUBLICATIONS

Clark–Lewis et al., "Structural requirements for interleukin–8 function identified by design of analogs and CXC chemokine hybrids," *J. Biol. Chem.* (1994) 269:16075–16081.

Cwirla et al., "Peptides on phage: a vast library of peptides for identifying ligands," *Proc. Natl. Acad. Sci. USA* (1990) 87:6378–6382.

Dawson et al., "Synthesis of proteins by native chemical Ligation," *Science* (1994) 266:776–779.

Devlin et al., "Random peptide libraries: a source of specific protein binding molecules," *Science* (1990) 249:404–406.

DeWitt et al., "Diversomers: an approach to nonpeptide, nonoligomeric chemical diversity," *Proc. Natl. Acad. Sci. U.S.A.* (1993) 90:6909–6913.

Dos Remedios et al., "Fluorescence resonance energy transfer measurements of distances in actin and myosin," *J. Muscle Res. Cell Motility* (1987) 8:97–117.

Fairclough and Cantor, "The use of singlet–singlet energy transfer to study macromolecular assemblies," *Meth. Enzymol.* (1978) 48:347–379.

Furka et al., Abstr. 14th Int. Congr. Biochem., Prague, Czechoslovakia, vol. 5, p. 47. Abstr. 10th Intl. Symp. Med. Chem., Budapest, Hungary, (1988), p. 288.

Gaertner et al., "Site–specific religation of G–CSF fragments through a thioester bond," *Bioconj. Chem.* (1994) 5(4) : 333–338.

Gallop et al.,"Applications of combinatorial technologies to drug discovery, 1," *J. Med. Chem.* (1994) 37:1233–1251.

Gauthier et al., "A new sensitive fluorogenic substrate for papain based on the sequence of the cystatin inhibitory site," *Arch. Biochem. Biophys.* (1993) 306:304–308.

Geahlen et al., "A general method for preparation of peptides biotinylated at the carboxy terminus," *Anal. Biochem.* (1992) 202:68–70.

Geysen et al., "Use of peptide synthesis to probe viral antigens for epitopes to a resolution of a single amino acid," *Proc. Nat. Acad. Sci. U.S.A.* (1984), 81:3998–4002.

Gordon et al., "Applications of combinatorial technologies to drug discovery, 2," *J. Med. Chem.* (1994) 37:1385–1401.

Houghten et al., " General method for the rapid solid–phase synthesis of large number of peptides," *Proc. Natl. Acad. Sci. U.S.A.* (1985) 82:5131–35.

Houghten et al., "Generation and use of synthetic peptide combinatorial libraries for basic research and drug discovery," *Nature* (1991) 354:84–86.

Hromas et al., "Cloning and characterization of exodus, a novel beta–chemokine," *Blood* (1997) 89(9): 3315–3322.

Lu et al., "Probing intermolecular main chain hydrogen bonding in serine proteinase–protein inhibitor complexes," *Biochemistry* (1997) 36(4): 673–679.

Maggiora et al., "A general method for the preparation of internally quenched fluorogenic protease substrates using solid–phase peptide synthesis," *J. Med. Chem.* (1992) 35:3727–3730.

Moos et al., "Recent advances in the generation of molecular diversity," *Annual Reports in Medicinal Chemistry* (1993) 28:315–324.

Muir and Kent, "The chemical synthesis of proteins," *Curr. Opin. Biotechnology* (1993) 4:420–427.

Needels et al., "Generation and screening of an oligonucleotide–encoded synthetic peptide library," *Proc. Natl. Acad. Sci. USA* (1993) 90:10700–10704.

Neote et al., "Molecular cloning, functional expression and signaling characteristics of a C–C chemokine receptor," *Cell* (1993) 72:415–425.

Oberlin et al., "The CXC chemokine SDF–1 is the ligand for LESTR/fusion and prevents infection by T–cell–line–adapted HIV–1," *Nature* (1996) 382:833–835.

Oppenheim, "Overview of chemokines," *Adv. Exp. Med. Biol.* (1993) 351:183–186.

Pavia et al., "The generation of molecular diversity," *Bioorganic and Medicinal Chem. Lett.* (1993) 3:387–396.

Peled et al., "Synthetic S–2 and H–5 segments of the Shaker K⁺ channel: secondary structure, membrane interaction, and assembly within phospholipid membranes," *Biochemistry* (1994) 33:7211–7219.

Proudfoot et al., "Extension of recombinant human RANTES by the retention of the initiating methionine produces a potent antagonist," *J.B.C.* (1996) 271:2599–2603.

Rajarathnam et al,. "Neutrophil activation by monomeric interleukin–8," *Science* (1994) 264:90–92.

Schnölzer et al., "In situ neutralization in Boc–chemistry solid phase peptide synthesis," *Int. J. Peptide Protein Res.* (1992) 40:180–193.

Schnölzer and Kent, "Constructing proteins by dovetailing unprotected synthetic peptides: backbone–engineered HIV protease," *Science* (1992) 256:221–225.

Siani, et al., "Rapid modular total chemical synthesis of chemokines based on genome sequence data," Poster #360, pp. 1–6, The 15$^{th}$ American Peptide Symposium, Nashville, Tennessee, U.S.A., Jun. 14–17, 1997.

Siani et al., "Rapid modular syntheis of SDF–1α with full biological activities," Poster, pp. 1–12, NMHCC, Chemokines and Host–Cell Interaction Conference, Baltimore, Maryland, U.S.A., Jan. 1997.

Simmons et al., "Potent inhibition of HIV–1 infectivity in macrophages and lymphocytes by a novel CCR5 antagonist," *Science* (1997) 276:276–279.

Smith G.P., "Filamentous fusion phage: novel expression vectors that display cloned antigens on the virion surface," *Science* (1985) 228:1315–1317.

Sticht et al., "Structure and activity of a chimeric interleukin–8–melanoma–growth–stimulatory–activity protein," *Eur. J. Biochem.* (1996) 235:26–35.

Strahilevits et al., "Spectrum of antimicrobial activity and assembly of dermaseptin–b and its precursor form in phospholipid membranes," *Biochemistry* (1994) 33:10951–10960.

Tam et al., "Peptide synthesis using unprotected peptides through orthogonal coupling methods," *Proc. Natl. Acad. Sci. USA* (1995) 92:12485–12489.

Ueda et al., "Chemically synthesized SDF–1 alpha analogue, N33A, is a potent chemotactic agent for CXCR4/Fusion/LESTR–expressing human leukocytes," *J. Biol. Chem.* (1997) 272:24966–24970.

Wernette–Hammond et al., "Receptor recoginition and specificity of interleukin–8 is determined by residues that cluster near a surface–accessible hydrophobic pocket," *J. Biol. Chem.* (1996) 271:8228–8235.

Wilken et al., "Solid Phase Chemical Ligation–A Paradigm for Post Genomic Pharmaceuticals," Fifth International Symposium on Solid Phase Synthesis and Combinatorial Chemical Libraries, London, England, U.K., (Sep. 4, 1997).

Wu et al., "Resonance energy transfer: methods and applications," *Analytical Biochem.* (1994) 218:1–13.

Zhang et al., "Preparation of functionally active cell–permeable peptides by single–step ligation of two peptide modules," *Proc. Natl. Acad. Sci. USA* (1998) 95:9184–9189.

Zuckermann et al., "Discovery of nanomolar ligands for 7–tranmembrane G–protein–coupled receptors from a diverse N– (substituted) glycine peptoid library," *J. Med. Chem.* (1994), 37:2678–2685.

Athanassopoulos et al., "Phase Change During Peptide Synthesis," *Innovation Perspect. Solid Phase Synth. Comb. Libr., Collect. Pap., Int. Symp., 4th* (1996) Meeting Date 1995, 243–246. Editor(s): Epton, Roger. Publisher: Mayflower Scientific, Birmingham, UK—*Chemical Abstracts*, vol. 127, No. 5.

Canne et al., "Extending the Applicability of Native Chemical Ligation," *J. Am. Chem. Soc.* 118:5891–5896 (1996).

Gaertner et al., "Chemical Ligation of Proteins and Other Macromolecules," *Peptide: Chemistry, Structure and Biology, Proc. Of the XIV Am. Pept. Symp.,* Jun. 1995, 18–23, Mayflower Sci. Ltd., England.

Lockhart et al., "The Cloning, Expression and Purification of Cervine Interleukin 2", *Cytokine*, (1996) 8(8): 603–612—*Chemical Abstracts*, vol. 125, No. 21.

Werlen et al., "Site–Specific Conjugation of an Enzyme and an Antibody Fragment," *Bioconjugate Chemistry*, (1994) 5(5): 411–417.

Yoshida et al., "Molecular Cloning of a Novel Human CC Chemokine EBI1–ligand Chemokine That Is a Specific Functional Ligand for EBI1, CCR7", *Journal of Biological Chemistry*, (1997) 272(21):13803–13809.

* cited by examiner

Generating Molecular Diversity using NCL*

CXC chemokine  SDF1α

CC chemokine  RANTES

8x N-terminal modules

4x C-terminal modules

Ligation at Xxx-Cys bond to generate hybrid molecule

*NCL=native chemical ligation

S'=-Pro & R=+Pro

FIGURE 3

CHEMOKINE PATTERNS AND MPBV

The two amino acids preceding the central cysteine are evaluated when designing improved agonists or antagonists.
MPBV* (vMIP-I or vMIP-II)

| | | | | | | | | | 10 | | | | | | | | | | 20 | | | |
|---|---|---|---|---|---|---|---|---|---|---|---|---|---|---|---|---|---|---|---|---|---|---|
| RANTES | S | P | Y | S | S | D | T | T | P | C | C | FA | Y | I | A | R | P | L | P | R | A | H | I |
| SDF1 | K | P | V | S | L | S | Y | R | C | P | C | R | F | F | E | S | H | V | A | R | A | N | V |
| MPBV* | G | A | S | W | H | R | P | D | K | C | C | LG | Y | Q | K | R | P | L | P | | Q | VL | L |
| | | | | | | | | | | | | | | ↑ | | | | * | | | | | * |

| | 24 | | | | | | 30 | | | | | | | | | | | 40 | | | | | |
|---|---|---|---|---|---|---|---|---|---|---|---|---|---|---|---|---|---|---|---|---|---|---|---|
| RANTES | K | E | Y | F | Y | T | | S | G | K | C | S | N | P | A | V | V | F | V | T | R | | K |
| SDF1 | K | L | H | K | I | L | N | T | P | N | C | A | L | | Q | I | V | A | R | L | K | N | N |
| MPBV* | S | S | W | Y | P | T | | S | Q | L | C | S | K | P | G | V | I | F | L | T | K | | R |
| | | | | | | | | | ↑ | ↑ | | | ↑ | | | * | | * | | * | | | |

| | | | | | | | | | | | | | | | | | | | | | 67 | | | |
|---|---|---|---|---|---|---|---|---|---|---|---|---|---|---|---|---|---|---|---|---|---|---|---|---|
| RANTES | N | R | Q | V | C | A | N | P | E | K | K | W | V | R | E | Y | I | N | S | L | E | M | S | | |
| SDF1 | N | R | Q | V | C | I | D | P | K | L | K | W | I | Q | E | Y | L | E | K | A | L | N | | | |
| MPBV* | G | R | Q | V | C | A | D | K | S | K | D | W | V | K | K | L | M | Q | Q | L | P | V | T | A | R |
| | | | | * | | * | | | | | | * | * | | | | | | | | | | | | |

* = Hydrophobic core side chains, highly conserved.
Bolded positions indicate conservation between all 3 or (MPBV and another).
↑ = Unique position, MPBV matches neither RANTES nor SDF1α.
All three N-terminii are unique. Likewise the two positions before the central cysteine are unique.

SEQUENCE LISTING

```
<160> NUMBER OF SEQ ID NOS: 54

<210> SEQ ID NO 1
<211> LENGTH: 81
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)..(8)
<223> OTHER INFORMATION: Xaa = Any Amino Acid
<220> FEATURE:
<221> NAME/KEY: SITE
<222> LOCATION: (10)
<223> OTHER INFORMATION: Xaa = Any Amino Acid
<220> FEATURE:
<221> NAME/KEY: SITE
<222> LOCATION: (16)..(21)
<223> OTHER INFORMATION: Xaa = Any Amino Acid
<220> FEATURE:
<221> NAME/KEY: SITE
<222> LOCATION: (28)..(29)
<223> OTHER INFORMATION: Xaa = Any Amino Acid
<220> FEATURE:
<221> NAME/KEY: SITE
<222> LOCATION: (35)
<223> OTHER INFORMATION: Xaa = Any Amino Acid
<220> FEATURE:
<221> NAME/KEY: SITE
<222> LOCATION: (40)..(41)
<223> OTHER INFORMATION: Xaa = Any Amino Acid
<220> FEATURE:
<221> NAME/KEY: SITE
<222> LOCATION: (46)..(50)
<223> OTHER INFORMATION: Xaa = Any Amino Acid
<220> FEATURE:
<221> NAME/KEY: SITE
<222> LOCATION: (54)..(55)
<223> OTHER INFORMATION: Xaa = Any Amino Acid
<220> FEATURE:
<221> NAME/KEY: SITE
<222> LOCATION: (57)..(59)
<223> OTHER INFORMATION: Xaa = Any Amino Acid
<220> FEATURE:
<221> NAME/KEY: SITE
<222> LOCATION: (66)..(77)
<223> OTHER INFORMATION: Xaa = Any Amino Acid

<400> SEQUENCE: 1

Xaa Xaa Xaa Xaa Xaa Xaa Xaa Xaa Cys Xaa Cys Leu Ile Val Met Xaa
 1               5                  10                  15

Xaa Xaa Xaa Xaa Xaa Leu Ile Val Met Phe Tyr Xaa Xaa Arg Lys Ser
                20                  25                  30

Glu Gln Xaa Leu Ile Val Met Xaa Xaa Leu Ile Val Met Xaa Xaa Xaa
            35                  40                  45

Xaa Xaa Ser Ala Gly Xaa Xaa Cys Xaa Xaa Xaa Glu Gln Leu Ile Val
        50                  55                  60

Met Xaa Xaa Xaa Xaa Xaa Xaa Xaa Xaa Xaa Xaa Xaa Cys Leu Asp
65                  70                  75                  80
```

Asn

```
<210> SEQ ID NO 2
<211> LENGTH: 82
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: SITE
<222> LOCATION: (1)..(9)
<223> OTHER INFORMATION: Xaa = Any Amino Acid
<220> FEATURE:
<221> NAME/KEY: SITE
<222> LOCATION: (19)..(24)
<223> OTHER INFORMATION: Xaa = Any Amino Acid
<220> FEATURE:
<221> NAME/KEY: SITE
<222> LOCATION: (29)..(32)
<223> OTHER INFORMATION: Xaa = Any Amino Acid
<220> FEATURE:
<221> NAME/KEY: SITE
<222> LOCATION: (38)..(39)
<223> OTHER INFORMATION: Xaa = Any Amino Acid
<220> FEATURE:
<221> NAME/KEY: SITE
<222> LOCATION: (41)..(43)
<223> OTHER INFORMATION: Xaa = Any Amino Acid
<220> FEATURE:
<221> NAME/KEY: SITE
<222> LOCATION: (52)..(53)
<223> OTHER INFORMATION: Xaa = Any Amino Acid
<220> FEATURE:
<221> NAME/KEY: SIMILAR
<222> LOCATION: (55)..(58)
<223> OTHER INFORMATION: Xaa = Any Amino Acid
<220> FEATURE:
<221> NAME/KEY: SITE
<222> LOCATION: (66)..(67)
<223> OTHER INFORMATION: Xaa = Any Amino Acid
<220> FEATURE:
<221> NAME/KEY: SITE
<222> LOCATION: (70)..(74)
<223> OTHER INFORMATION: Xaa = Any Amino Acid
<220> FEATURE:
<221> NAME/KEY: SITE
<222> LOCATION: (80)..(81)
<223> OTHER INFORMATION: Xaa = Any Amino Acid

<400> SEQUENCE: 2

Xaa Xaa Xaa Xaa Xaa Xaa Xaa Xaa Xaa Cys Cys Leu Ile Val Met Phe
 1               5                  10                  15

Tyr Thr Xaa Xaa Xaa Xaa Xaa Xaa Leu Ile Val Met Xaa Xaa Xaa Xaa
                20                  25                  30

Leu Ile Val Met Phe Xaa Xaa Tyr Xaa Xaa Xaa Gly Ser Thr Asn Gly
            35                  40                  45

Ser Thr Asn Xaa Xaa Cys Xaa Xaa Xaa Xaa Ser Ala Gly Leu Ile Val
        50                  55                  60

Met Xaa Xaa Phe Leu Xaa Xaa Xaa Xaa Arg Lys Thr Met Phe Xaa
 65                  70                  75                  80

Xaa Cys

<210> SEQ ID NO 3
<211> LENGTH: 71
<212> TYPE: PRT
<213> ORGANISM: Artificial Sequence
<220> FEATURE:
<223> OTHER INFORMATION: Description of Artificial Sequence: Synthetic

<400> SEQUENCE: 3
```

-continued

Ala Gly Ser Leu Val Ser Tyr Thr Pro Asn Ser Cys Cys Tyr Gly Phe
 1               5                  10                  15

Gln Gln His Pro Pro Val Gln Ile Leu Lys Glu Trp Tyr Pro Thr
            20                  25                  30

Ser Pro Ala Cys Pro Lys Pro Gly Val Ile Leu Leu Thr Lys Arg Gly
            35                  40                  45

Arg Gln Ile Cys Ala Asp Pro Ser Lys Asn Trp Val Arg Gln Leu Met
        50                  55                  60

Gln Arg Leu Pro Ala Ile Ala
 65                  70

<210> SEQ ID NO 4
<211> LENGTH: 74
<212> TYPE: PRT
<213> ORGANISM: Artificial Sequence
<220> FEATURE:
<223> OTHER INFORMATION: Description of Artificial Sequence: Synthetic

<400> SEQUENCE: 4

Gly Asp Thr Leu Gly Ala Ser Trp His Arg Pro Asp Lys Cys Cys Leu
 1               5                  10                  15

Gly Tyr Gln Lys Arg Pro Leu Pro Gln Val Leu Leu Ser Ser Trp Tyr
            20                  25                  30

Pro Thr Ser Gln Leu Cys Ser Lys Pro Gly Val Ile Phe Leu Thr Lys
            35                  40                  45

Arg Gly Arg Gln Val Cys Ala Asp Lys Ser Lys Asp Trp Val Lys Lys
        50                  55                  60

Leu Met Gln Gln Leu Pro Val Thr Ala Arg
 65                  70

<210> SEQ ID NO 5
<211> LENGTH: 72
<212> TYPE: PRT
<213> ORGANISM: Artificial Sequence
<220> FEATURE:
<223> OTHER INFORMATION: Description of Artificial Sequence: Synthetic

<400> SEQUENCE: 5

Ala Gly Ser Leu Val Ser Tyr Thr Pro Asn Ser Cys Cys Tyr Gly Phe
 1               5                  10                  15

Gln Gln His Pro Pro Val Gln Ile Leu Lys Glu Trp Tyr Pro Thr
            20                  25                  30

Ser Pro Ala Cys Ser Lys Pro Gly Val Ile Phe Leu Thr Lys Arg Gly
            35                  40                  45

Arg Gln Val Cys Ala Asp Lys Ser Lys Asp Trp Val Lys Lys Leu Met
        50                  55                  60

Gln Gln Leu Pro Val Thr Ala Arg
 65                  70

<210> SEQ ID NO 6
<211> LENGTH: 73
<212> TYPE: PRT
<213> ORGANISM: Artificial Sequence
<220> FEATURE:
<223> OTHER INFORMATION: Description of Artificial Sequence: Synthetic

<400> SEQUENCE: 6

Gly Asp Thr Leu Gly Ala Ser Trp His Arg Pro Asp Lys Cys Cys Leu
 1               5                  10                  15

Gly Tyr Gln Lys Arg Pro Leu Pro Gln Val Leu Leu Ser Ser Trp Tyr
                20                  25                  30

Pro Thr Ser Gln Leu Cys Pro Lys Pro Gly Val Ile Leu Leu Thr Lys
            35                  40                  45

Arg Gly Arg Gln Ile Cys Ala Asp Pro Ser Lys Asn Trp Val Arg Gln
        50                  55                  60

Leu Met Gln Arg Leu Pro Ala Ile Ala
65                  70

<210> SEQ ID NO 7
<211> LENGTH: 93
<212> TYPE: PRT
<213> ORGANISM: Artificial Sequence
<220> FEATURE:
<223> OTHER INFORMATION: Description of Artificial Sequence: Synthetic

<400> SEQUENCE: 7

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 8
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 8

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn
65

<210> SEQ ID NO 9
<211> LENGTH: 91
<212> TYPE: PRT
<213> ORGANISM: Artificial Sequence
<220> FEATURE:
<223> OTHER INFORMATION: Description of Artificial Sequence: Synthetic

<400> SEQUENCE: 9

Met Lys Val Ser Ala Ala Arg Leu Ala Val Ile Leu Ile Ala Thr Ala
1               5                   10                  15

Leu Cys Ala Pro Ala Ser Ala Ser Pro Tyr Ser Ser Asp Thr Thr Pro

```
            20                  25                  30
Cys Cys Phe Ala Tyr Ile Ala Arg Pro Leu Pro Arg Ala His Ile Lys
        35                  40                  45

Glu Tyr Phe Tyr Thr Ser Gly Lys Cys Ser Asn Pro Ala Val Val Phe
     50                  55                  60

Val Thr Arg Lys Asn Arg Gln Val Cys Ala Asn Pro Glu Lys Lys Trp
 65                  70                  75                  80

Val Arg Glu Tyr Ile Asn Ser Leu Glu Met Ser
                 85                  90

<210> SEQ ID NO 10
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 10

Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
             20                  25                  30

Lys Cys Ser Asn Pro Ala Val Val Phe Val Thr Arg Lys Asn Arg Gln
         35                  40                  45

Val Cys Ala Asn Pro Glu Lys Lys Trp Val Arg Glu Tyr Ile Asn Ser
     50                  55                  60

Leu Glu Met Ser
 65

<210> SEQ ID NO 11
<211> LENGTH: 33
<212> TYPE: PRT
<213> ORGANISM: Artificial Sequence
<220> FEATURE:
<223> OTHER INFORMATION: Description of Artificial Sequence: Synthetic

<400> SEQUENCE: 11

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
             20                  25                  30

Asn

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 12

Lys Pro Val Ser Leu Ser Tyr Arg Cys Cys Arg Phe Phe Glu Ser His
 1               5                  10                  15

Val Ala Arg Ala Asn Val Lys His Leu Lys Ile Leu Asn Thr Pro Asn
             20                  25                  30

<210> SEQ ID NO 13
<211> LENGTH: 33
<212> TYPE: PRT
<213> ORGANISM: Artificial Sequence
<220> FEATURE:
```

<223> OTHER INFORMATION: Description of Artificial Sequence: Synthetic

<400> SEQUENCE: 13

Lys Pro Val Ser Leu Ser Tyr Arg Cys Pro Cys Phe Ala Tyr Ile Ala
 1               5                  10                  15
Arg Pro Leu Pro Arg Ala His Ile Lys Glu Tyr Phe Tyr Thr Ser Gly
            20                  25                  30
Lys

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: Synthetic

<400> SEQUENCE: 14

Lys Pro Val Ser Leu Ser Tyr Arg Cys Cys Phe Ala Tyr Ile Ala Arg
 1               5                  10                  15
Pro Leu Pro Arg Ala His Ile Lys Glu Tyr Phe Tyr Thr Ser Gly Lys
            20                  25                  30

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic

<400> SEQUENCE: 15

Ser Pro Tyr Ser Ser Asp Thr Thr Pro Cys Cys Phe Ala Tyr Ile Ala
 1               5                  10                  15
Arg Pro Leu Pro Arg Ala His Ile Lys Glu Tyr Phe Tyr Thr Ser Gly
            20                  25                  30
Lys

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic

<400> SEQUENCE: 16

Ser Pro Tyr Ser Ser Asp Thr Thr Pro Cys Pro Cys Phe Ala Tyr Ile
 1               5                  10                  15
Ala Arg Pro Leu Pro Arg Ala His Ile Lys Glu Tyr Phe Tyr Thr Ser
            20                  25                  30
Gly Lys

<210> SEQ ID NO 17
<211> LENGTH: 33
<212> TYPE: PRT
<213> ORGANISM: Artificial Sequence
<220> FEATURE:
<223> OTHER INFORMATION: Description of Artificial Sequence: Synthetic

<400> SEQUENCE: 17

Ser Pro Tyr Ser Ser Asp Thr Thr Pro Cys Cys Arg Phe Phe Glu Ser
 1               5                  10                  15
His Val Ala Arg Ala Asn Val Lys His Leu Lys Ile Leu Asn Thr Pro
            20                  25                  30

Asn

<210> SEQ ID NO 18
<211> LENGTH: 34
<212> TYPE: PRT
<213> ORGANISM: Artificial Sequence
<220> FEATURE:
<223> OTHER INFORMATION: Description of Artificial Sequence: Synthetic

<400> SEQUENCE: 18

Ser Pro Tyr Ser Ser Asp Thr Thr Pro Cys Pro Cys Arg Phe Phe Glu
 1               5                  10                  15

Ser His Val Ala Arg Ala Asn Val Lys His Leu Lys Ile Leu Asn Thr
            20                  25                  30

Pro Asn

<210> SEQ ID NO 19
<211> LENGTH: 34
<212> TYPE: PRT
<213> ORGANISM: Artificial Sequence
<220> FEATURE:
<223> OTHER INFORMATION: Description of Artificial Sequence: Synthetic

<400> SEQUENCE: 19

Cys Ala Leu Gln Ile Val Ala Arg Leu Lys Asn Asn Asn Arg Gln Val
 1               5                  10                  15

Cys Ile Asp Pro Lys Leu Lys Trp Ile Gln Glu Tyr Leu Glu Lys Ala
            20                  25                  30

Leu Asn

<210> SEQ ID NO 20
<211> LENGTH: 35
<212> TYPE: PRT
<213> ORGANISM: Artificial Sequence
<220> FEATURE:
<223> OTHER INFORMATION: Description of Artificial Sequence: Synthetic

<400> SEQUENCE: 20

Cys Ala Leu Gln Ile Val Ala Arg Leu Lys Asn Asn Asn Arg Gln Val
 1               5                  10                  15

Cys Ala Asn Pro Glu Lys Lys Trp Val Arg Glu Tyr Ile Asn Ser Leu
            20                  25                  30

Glu Met Ser
        35

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: Synthetic

<400> SEQUENCE: 21

Cys Ser Asn Pro Ala Val Val Phe Val Thr Arg Lys Asn Arg Gln Val
 1               5                  10                  15

Cys Ile Asp Pro Lys Leu Lys Trp Ile Gln Glu Tyr Leu Glu Lys Ala
            20                  25                  30

Leu Asn

<210> SEQ ID NO 22
<211> LENGTH: 35

<212> TYPE: PRT
<213> ORGANISM: Artificial Sequence
<220> FEATURE:
<223> OTHER INFORMATION: Description of Artificial Sequence: Synthetic

<400> SEQUENCE: 22

Cys Ser Asn Pro Ala Val Val Phe Val Thr Arg Lys Asn Arg Gln Val
 1               5                  10                  15

Cys Ala Asn Pro Glu Lys Lys Trp Val Arg Glu Tyr Ile Asn Ser Leu
             20                  25                  30

Glu Met Ser
         35

<210> SEQ ID NO 23
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 23

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
     50                  55                  60

Ala Leu Asn
 65

<210> SEQ ID NO 24
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 24

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ala Asn Pro Glu Lys Lys Trp Val Arg Glu Tyr Ile Asn Ser
     50                  55                  60

Leu Glu Met Ser
 65

<210> SEQ ID NO 25
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 25

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
            20                  25                  30

Asn Cys Ser Asn Pro Ala Val Val Phe Val Thr Arg Lys Asn Arg Gln
            35                  40                  45

Val Cys Ile Asp Pro Lys Leu Lys Trp Ile Gln Glu Tyr Leu Glu Lys
        50                  55                  60

Ala Leu Asn
 65

<210> SEQ ID NO 26
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 26

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
            20                  25                  30

Asn Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Met Ser
 65

<210> SEQ ID NO 27
<211> LENGTH: 66
<212> TYPE: PRT
<213> ORGANISM: Artificial Sequence
<220> FEATURE:
<223> OTHER INFORMATION: Description of Artificial Sequence: Synthetic

<400> SEQUENCE: 27

Lys Pro Val Ser Leu Ser Tyr Arg Cys Cys Arg Phe Phe Glu Ser His
 1               5                  10                  15

Val Ala Arg Ala Asn Val Lys His Leu Lys Ile Leu Asn Thr Pro Asn
            20                  25                  30

Cys Ala Leu Gln Ile Val Ala Arg Leu Lys Asn Asn Asn Arg Gln Val
            35                  40                  45

Cys Ile Asp Pro Lys Leu Lys Trp Ile Gln Glu Tyr Leu Glu Lys Ala
        50                  55                  60

Leu Asn
 65

<210> SEQ ID NO 28
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 28

Lys Pro Val Ser Leu Ser Tyr Arg Cys Cys Arg Phe Phe Glu Ser His
 1               5                  10                  15

Val Ala Arg Ala Asn Val Lys His Leu Lys Ile Leu Asn Thr Pro Asn
            20                  25                  30

Cys Ala Leu Gln Ile Val Ala Arg Leu Lys Asn Asn Asn Arg Gln Val

```
                35              40              45

Cys Ala Asn Pro Glu Lys Lys Trp Val Arg Glu Tyr Ile Asn Ser Leu
         50                  55                  60

Glu Met Ser
 65

<210> SEQ ID NO 29
<211> LENGTH: 66
<212> TYPE: PRT
<213> ORGANISM: Artificial Sequence
<220> FEATURE:
<223> OTHER INFORMATION: Description of Artificial Sequence: Synthetic

<400> SEQUENCE: 29

Lys Pro Val Ser Leu Ser Tyr Arg Cys Cys Arg Phe Phe Glu Ser His
 1               5                  10                  15

Val Ala Arg Ala Asn Val Lys His Leu Lys Ile Leu Asn Thr Pro Cys
                20                  25                  30

Asn Ser Asn Pro Ala Val Val Phe Val Thr Arg Lys Asn Arg Gln Val
             35                  40                  45

Cys Ile Asp Pro Lys Leu Lys Trp Ile Gln Glu Tyr Leu Glu Lys Ala
         50                  55                  60

Leu Asn
 65

<210> SEQ ID NO 30
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 30

Lys Pro Val Ser Leu Ser Tyr Arg Cys Cys Arg Phe Phe Glu Ser His
 1               5                  10                  15

Val Ala Arg Ala Asn Val Lys His Leu Lys Ile Leu Asn Thr Pro Asn
                20                  25                  30

Cys Ser Asn Pro Ala Val Val Phe Val Thr Arg Lys Asn Arg Gln Val
             35                  40                  45

Cys Ala Asn Pro Glu Lys Lys Trp Val Arg Glu Tyr Ile Asn Ser Leu
         50                  55                  60

Glu Met Ser
 65

<210> SEQ ID NO 31
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 31

Lys Pro Val Ser Leu Ser Tyr Arg Cys Pro Cys Phe Ala Tyr Ile Ala
 1               5                  10                  15

Arg Pro Leu Pro Arg Ala His Ile Lys Glu Tyr Phe Tyr Thr Ser Gly
                20                  25                  30

Lys Cys Ala Leu Gln Ile Val Ala Arg Leu Lys Asn Asn Asn Arg Gln
             35                  40                  45

Val Cys Ile Asp Pro Lys Leu Lys Trp Ile Gln Glu Tyr Leu Glu Lys
         50                  55                  60
```

Ala Leu Asn
65

<210> SEQ ID NO 32
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 32

Lys Pro Val Ser Leu Ser Tyr Arg Cys Pro Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ala Leu Gln Ile Val Ala Arg Leu Lys Asn Asn Asn Arg Gln
        35                  40                  45

Val Cys Ala Asn Pro Glu Lys Lys Trp Val Arg Glu Tyr Ile Asn Ser
    50                  55                  60

Leu Glu Met Ser
65

<210> SEQ ID NO 33
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 33

Lys Pro Val Ser Leu Ser Tyr Arg Cys Pro Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ile Asp Pro Lys Leu Lys Trp Ile Gln Glu Tyr Leu Glu Lys
    50                  55                  60

Ala Leu Asn
65

<210> SEQ ID NO 34
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 34

Lys Pro Val Ser Leu Ser Tyr Arg Cys Pro Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65

```
<210> SEQ ID NO 35
<211> LENGTH: 66
<212> TYPE: PRT
<213> ORGANISM: Artificial Sequence
<220> FEATURE:
<223> OTHER INFORMATION: Description of Artificial Sequence: Synthetic

<400> SEQUENCE: 35

Lys Pro Val Ser Leu Ser Tyr Arg Cys Cys Phe Ala Tyr Ile Ala Arg
 1               5                  10                  15

Pro Leu Pro Arg Ala His Ile Lys Glu Tyr Phe Tyr Thr Ser Gly Lys
             20                  25                  30

Cys Ala Leu Gln Ile Val Ala Arg Leu Lys Asn Asn Asn Arg Gln Val
         35                  40                  45

Cys Ile Asp Pro Lys Leu Lys Trp Ile Gln Glu Tyr Leu Glu Lys Ala
     50                  55                  60

Leu Asn
 65

<210> SEQ ID NO 36
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 36

Lys Pro Val Ser Leu Ser Tyr Arg Cys Cys Phe Ala Tyr Ile Ala Arg
 1               5                  10                  15

Pro Leu Pro Arg Ala His Ile Lys Glu Tyr Phe Tyr Thr Ser Gly Lys
             20                  25                  30

Cys Ala Leu Gln Ile Val Ala Arg Leu Lys Asn Asn Asn Arg Gln Val
         35                  40                  45

Cys Ala Asn Pro Glu Lys Lys Trp Val Arg Glu Tyr Ile Asn Ser Leu
     50                  55                  60

Glu Met Ser
 65

<210> SEQ ID NO 37
<211> LENGTH: 66
<212> TYPE: PRT
<213> ORGANISM: Artificial Sequence
<220> FEATURE:
<223> OTHER INFORMATION: Description of Artificial Sequence: Synthetic

<400> SEQUENCE: 37

Lys Pro Val Ser Leu Ser Tyr Arg Cys Cys Phe Ala Tyr Ile Ala Arg
 1               5                  10                  15

Pro Leu Pro Arg Ala His Ile Lys Glu Tyr Phe Tyr Thr Ser Gly Lys
             20                  25                  30

Cys Ser Asn Pro Ala Val Val Phe Val Thr Arg Lys Asn Arg Gln Val
         35                  40                  45

Cys Ile Asp Pro Lys Leu Lys Trp Ile Gln Glu Tyr Leu Glu Lys Ala
     50                  55                  60

Leu Asn
 65

<210> SEQ ID NO 38
<211> LENGTH: 67
<212> TYPE: PRT
```

<213> ORGANISM: Artificial Sequence
<220> FEATURE:
<223> OTHER INFORMATION: Description of Artificial Sequence: Synthetic

<400> SEQUENCE: 38

Lys Pro Val Ser Leu Ser Tyr Arg Cys Cys Phe Ala Tyr Ile Ala Arg
 1               5                  10                  15

Pro Leu Pro Arg Ala His Ile Lys Glu Tyr Phe Tyr Thr Ser Gly Lys
            20                  25                  30

Cys Ser Asn Pro Ala Val Val Phe Val Thr Arg Lys Asn Arg Gln Val
        35                  40                  45

Cys Ala Asn Pro Glu Lys Lys Trp Val Arg Glu Tyr Ile Asn Ser Leu
    50                  55                  60

Glu Met Ser
 65

<210> SEQ ID NO 39
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 39

Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
            20                  25                  30

Lys Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn
 65

<210> SEQ ID NO 40
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 40

Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
            20                  25                  30

Lys Cys Ala Leu Gln Ile Val Ala Arg Leu Lys Asn Asn Asn Arg Gln
        35                  40                  45

Val Cys Ala Asn Pro Glu Lys Lys Trp Val Arg Glu Tyr Ile Asn Ser
    50                  55                  60

Leu Glu Met Ser
 65

<210> SEQ ID NO 41
<211> LENGTH: 67
<212> TYPE: PRT
<213> ORGANISM: Artificial Sequence
<220> FEATURE:
<223> OTHER INFORMATION: Description of Artificial Sequence: Synthetic

```
<400> SEQUENCE: 41

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ile Asp Pro Lys Leu Lys Trp Ile Gln Glu Tyr Leu Glu Lys
    50                  55                  60

Ala Leu Asn
65

<210> SEQ ID NO 42
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 42

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65

<210> SEQ ID NO 43
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 43

Ser Pro Tyr Ser Ser Asp Thr Thr Pro Cys Pro Cys Phe Ala Tyr Ile
1               5                   10                  15

Ala Arg Pro Leu Pro Arg Ala His Ile Lys Glu Tyr Phe Tyr Thr Ser
            20                  25                  30

Gly Lys Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn
65

<210> SEQ ID NO 44
<211> LENGTH: 69
<212> TYPE: PRT
<213> ORGANISM: Artificial Sequence
<220> FEATURE:
<223> OTHER INFORMATION: Description of Artificial Sequence: Synthetic

<400> SEQUENCE: 44

Ser Pro Tyr Ser Ser Asp Thr Thr Pro Cys Pro Cys Phe Ala Tyr Ile
1               5                   10                  15
```

```
Ala Arg Pro Leu Pro Arg Ala His Ile Lys Glu Tyr Phe Tyr Thr Ser
            20                  25                  30

Gly Lys Cys Ala Leu Gln Ile Val Ala Arg Leu Lys Asn Asn Asn Arg
        35                  40                  45

Gln Val Cys Ala Asn Pro Glu Lys Lys Trp Val Arg Glu Tyr Ile Asn
    50                  55                  60

Ser Leu Glu Met Ser
65

<210> SEQ ID NO 45
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 45

Ser Pro Tyr Ser Ser Asp Thr Thr Pro Cys Pro Cys Phe Ala Tyr Ile
1               5                   10                  15

Ala Arg Pro Leu Pro Arg Ala His Ile Lys Glu Tyr Phe Tyr Thr Ser
            20                  25                  30

Gly Lys Cys Ser Asn Pro Ala Val Val Phe Val Thr Arg Lys Asn Arg
        35                  40                  45

Gln Val Cys Ile Asp Pro Lys Leu Lys Trp Ile Gln Glu Tyr Leu Glu
    50                  55                  60

Lys Ala Leu Asn
65

<210> SEQ ID NO 46
<211> LENGTH: 69
<212> TYPE: PRT
<213> ORGANISM: Artificial Sequence
<220> FEATURE:
<223> OTHER INFORMATION: Description of Artificial Sequence: Synthetic

<400> SEQUENCE: 46

Ser Pro Tyr Ser Ser Asp Thr Thr Pro Cys Pro Cys Phe Ala Tyr Ile
1               5                   10                  15

Ala Arg Pro Leu Pro Arg Ala His Ile Lys Glu Tyr Phe Tyr Thr Ser
            20                  25                  30

Gly Lys Cys Ser Asn Pro Ala Val Val Phe Val Thr Arg Lys Asn Arg
        35                  40                  45

Gln Val Cys Ala Asn Pro Glu Lys Lys Trp Val Arg Glu Tyr Ile Asn
    50                  55                  60

Ser Leu Glu Met Ser
65

<210> SEQ ID NO 47
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 47

Ser Pro Tyr Ser Ser Asp Thr Thr Pro Cys Cys Arg Phe Phe Glu Ser
1               5                   10                  15

His Val Ala Arg Ala Asn Val Lys His Leu Lys Ile Leu Asn Thr Pro
            20                  25                  30
```

```
Asn Cys Ala Leu Gln Ile Val Ala Arg Leu Lys Asn Asn Arg Gln
        35                  40                  45

Val Cys Ile Asp Pro Lys Leu Lys Trp Ile Gln Glu Tyr Leu Glu Lys
    50                  55                  60

Ala Leu Asn
 65

<210> SEQ ID NO 48
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 48

Ser Pro Tyr Ser Ser Asp Thr Thr Pro Cys Cys Arg Phe Phe Glu Ser
 1               5                  10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Arg Gln
        35                  40                  45

Val Cys Ala Asn Pro Glu Lys Lys Trp Val Arg Glu Tyr Ile Asn Ser
    50                  55                  60

Leu Glu Met Ser
 65

<210> SEQ ID NO 49
<211> LENGTH: 67
<212> TYPE: PRT
<213> ORGANISM: Artificial Sequence
<220> FEATURE:
<223> OTHER INFORMATION: Description of Artificial Sequence: Synthetic

<400> SEQUENCE: 49

Ser Pro Tyr Ser Ser Asp Thr Thr Pro Cys Cys Arg Phe Phe Glu Ser
 1               5                  10                  15

His Val Ala Arg Ala Asn Val Lys His Leu Lys Ile Leu Asn Thr Pro
                20                  25                  30

Asn Cys Ser Asn Pro Ala Val Val Phe Val Thr Arg Lys Asn Arg Gln
        35                  40                  45

Val Cys Ile Asp Pro Lys Leu Lys Trp Ile Gln Glu Tyr Leu Glu Lys
    50                  55                  60

Ala Leu Asn
 65

<210> SEQ ID NO 50
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 50

Ser Pro Tyr Ser Ser Asp Thr Thr Pro Cys Cys Arg Phe Phe Glu Ser
 1               5                  10                  15

His Val Ala Arg Ala Asn Val Lys His Leu Lys Ile Leu Asn Thr Pro
                20                  25                  30

Asn Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
```

```
                50                   55                   60
Leu Glu Met Ser
 65

<210> SEQ ID NO 51
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 51

Ser Pro Tyr Ser Ser Asp Thr Thr Pro Cys Pro Cys Arg Phe Phe Glu
  1               5                  10                  15

Ser His Val Ala Arg Ala Asn Val Lys His Leu Lys Ile Leu Asn Thr
             20                  25                  30

Pro Asn Cys Ala Leu Gln Ile Val Ala Arg Leu Lys Asn Asn Asn Arg
         35                  40                  45

Gln Val Cys Ile Asp Pro Lys Leu Lys Trp Ile Gln Glu Tyr Leu Glu
     50                  55                  60

Lys Ala Leu Asn
 65

<210> SEQ ID NO 52
<211> LENGTH: 69
<212> TYPE: PRT
<213> ORGANISM: Artificial Sequence
<220> FEATURE:
<223> OTHER INFORMATION: Description of Artificial Sequence: Synthetic

<400> SEQUENCE: 52

Ser Pro Tyr Ser Ser Asp Thr Thr Pro Cys Pro Cys Arg Phe Phe Glu
  1               5                  10                  15

Ser His Val Ala Arg Ala Asn Val Lys His Leu Lys Ile Leu Asn Thr
             20                  25                  30

Pro Asn Cys Ala Leu Gln Ile Val Ala Arg Leu Lys Asn Asn Asn Arg
         35                  40                  45

Gln Val Cys Ala Asn Pro Glu Lys Lys Trp Val Arg Glu Tyr Ile Asn
     50                  55                  60

Ser Leu Glu Met Ser
 65

<210> SEQ ID NO 53
<211> LENGTH: 68
<212> TYPE: PRT
<213> ORGANISM: Artificial Sequence
<220> FEATURE:
<223> OTHER INFORMATION: Description of Artificial Sequence: Synthetic

<400> SEQUENCE: 53

Ser Pro Tyr Ser Ser Asp Thr Thr Pro Cys Pro Cys Arg Phe Phe Glu
  1               5                  10                  15

Ser His Val Ala Arg Ala Asn Val Lys His Leu Lys Ile Leu Asn Thr
             20                  25                  30

Pro Asn Cys Ser Asn Pro Ala Val Val Phe Val Thr Arg Lys Asn Arg
         35                  40                  45

Gln Val Cys Ile Asp Pro Lys Leu Lys Trp Ile Gln Glu Tyr Leu Glu
     50                  55                  60

Lys Ala Leu Asn
 65
```

```
<210> SEQ ID NO 54
<211> LENGTH: 69
<212> TYPE: PRT
<213> ORGANISM: Artificial Sequence
<220> FEATURE:
<223> OTHER INFORMATION: Description of Artificial Sequence: Synthetic

<400> SEQUENCE: 54

Ser Pro Tyr Ser Ser Asp Thr Thr Pro Cys Pro Cys Arg Phe Phe Glu
 1               5                  10                  15

Ser His Val Ala Arg Ala Asn Val Lys His Leu Lys Ile Leu Asn Thr
            20                  25                  30

Pro Asn Cys Ser Asn Pro Ala Val Val Phe Val Thr Arg Lys Asn Arg
        35                  40                  45

Gln Val Cys Ala Asn Pro Glu Lys Lys Trp Val Arg Glu Tyr Ile Asn
    50                  55                  60

Ser Leu Glu Met Ser
65
```

MODULAR PROTEIN LIBRARIES AND METHODS OF PREPARATION

CROSS REFERENCE TO RELATED APPLICATIONS

This application claims benefit to provisional application U.S. Ser. No. 60/057,620, filed Sep. 4, 1997.

FIELD OF THE INVENTION

The present invention relates to modular protein molecules and modular protein libraries obtained by cross-over synthesis of two or more functional protein modules derived from different parent protein molecules.

BACKGROUND OF THE INVENTION

Chemical leads for the pharmaceutical industry are currently identified through rational design and/or mass screening. The recent introduction of high throughput, automated screening technologies has permitted evaluation of hundreds of thousands of individual test molecules against a large number of targets. However, the source, diversity and functionality of large chemical libraries still remains a limitation in identifying new leads. Compound libraries commonly used in mass screening consist of either a historical collection of synthesized compounds or natural product collections. Historical collections contain a limited number of diverse structures and represent only a small fraction of diversity possibilities. They also contain a limited number of biologically useful compounds. Natural products are limited by the structural complexity of the leads identified and the difficulty of reducing them to useful pharmaceutical agents (e.g., taxol).

Methods available for generating synthetic compound libraries differ considerably in the types and numbers of compounds prepared, and whether the compounds are obtained as single structurally defined entities or as large mixtures. New compound libraries have been obtained through rapid chemical and biological synthesis (Moos et al., *Ann. Rep. Med. Chem.* (1993) 28:315–324; Pavia et al., *Bioorganic Medicinal Chem. Lett.* (1993) 3:387–96; Gallop et al., *J. Med. Chem.*, (1994) 37:1233–1251; Gordon et al, *J. Med. Chem.* (1994) 37:1385–1401). Peptide libraries containing hundreds to millions of small to medium size peptides have been made using "pin technology" representing a method that generates libraries of single compounds in a spatially-differentiated manner (Geysen et al., *Proc. Nat. Acad. Sci. U.S.A.* (1984), 81:3998–4002). The "spilt pool" method provides an alternative approach to preparing large mixtures of peptides and other classes of molecules (Furka et al., Abstr. 14th Int. Congr. Biochem., Prague, Czechoslovakia, Vol 5, pg 47. Abstr. 10th Intl. Symp. Med. Chem., Budapest, Hungary, (1988), pg 288; Houghten et al., *Proc. Natl. Acad. Sci. U.S.A.* (1985) 82:5131–35). Peptide libraries also have been produced by the "tea-bag" method in which small amounts of resins representing individual peptides are enclosed in porous polypropylene containers (Houghten et al., *Nature* (1991) 354:84–86). The bags are immersed in individual solutions of the appropriate activated amino acids while deprotections and washings are carried out by mixing all the bags together. The bags are then reseparated for subsequent coupling steps (the split-pool method). Removal of the peptides from the resins affords peptides in soluble form. It is possible to rapidly prepare a collection of libraries which represents, for example, all 64 million naturally-occurring hexapeptides and identify an optimal peptide ligand for any ligate of interest. Libraries of peptides also have been prepared on polymeric beads by the split-pool method and incubated with a tagged ligate. Ligates with bound peptides are identified by visual inspection, physically removed, and microsequenced (Lam et al., *Nature* (1991) 354:82–84). The approach also can incorporate cleavable linkers on each bead where, after exposure to cleaving reagent, the beads release a portion of their peptides into solution for biological assay and still retain sufficient peptide on the bead for microsequencing. The pin, split-pool, and tea-bag methods and libraries generated therefrom are limited to relatively small peptides amenable to this technology and the difficulty in identifying functional peptides of interest.

Peptide libraries also have been prepared in which an "identifier" tag is attached to a solid support material coincident with each monomer using a split-pool synthesis procedure. The structure of the molecule on any bead identified through screening is obtained by decoding the identifier tags. Numerous methods of tagging the beads have now been reported. These include the use of single stranded oligonucleotides which have the advantage of being used as identifying tags as well as allowing for enrichment through the use for PCR amplification (Brenner et al., *Proc. Natl. Acad. Sci. U.S.A.* (1992) 89:5381–5383; Nielsen et al., *J. Am. Chem. Soc.* (1993) 115:9812–9813; Needels et al., *Proc. Natl. Acad. Sci. USA* (1993) 90:10700–10704). The use of halocarbon derivatives which are released from the active beads through photolysis and sequenced using electron capture capillary chromatography has also been described (Gallop et al., *Journal of Medicinal Chemistry*, (1994) 37:1233–1251). While identifier tags aid screening of large peptide libraries, peptides are likely to have limited therapeutic applicability when modulation of receptor activity involved in a particular disorder require interaction with whole proteins, or protein complexes.

Phage libraries containing tens of millions of filamentous phage clones have been used as a biological source for generating peptide libraries, with each clone displaying a unique peptide sequence on the bacteriophage surface (Smith G. P., *Science* (1985) 228:1315–1317; Cwirla et al., *Proc. Natl. Acad. Sci. USA* (1990) 87:6378–6382; Devlin et al., *Science* (1990) 249:404–406). In this method, the phage genome contains the DNA sequence encoding for the peptide. The ligate of interest is used to affinity purify phage that display binding peptides, the phage propagated in *E. coli*, and the amino acid sequences of the peptides displayed on the phage are identified by sequencing the corresponding coding region of the viral DNA. Tens of millions of peptides can be rapidly surveyed for binding. Initial libraries of short peptides generally afford relatively weak ligands. Longer epitope regions and/or constrained epitopes also have been prepared. Phage technology also has effectively been applied to proteins and antibodies demonstrating that protein domains can fold properly on the surface of phage. A limitation of this method is that only naturally occurring amino acids can be used and little is known about the effect of the phage environment, as well as contaminants from cellular debris and phage.

Peptoid libraries have been created which represent a collection of peptides having N-substituted glycines as peptoid monomers (Zuckermann et al., *J. Med. Chem.* (1994) 37:2678–2685; Bunin et al., *J. Am. Chem. Soc.* (1992) 114:10997–10998; DeWitt et al., *Proc. Natl. Acad. Sci. U.S.A.* (1993) 90:6909–6913; Bunin et al., *Proc. Natl. Acad. Sci. USA* (1993) 91:4708–4712; Hogan et al. WO 94/01102). Structures of the resulting compounds are unique, likely to display unique binding properties, and incorporate important functionalities of peptides in a novel backbone. The methods generate single structurally well defined molecules in a solution format after cleavage from a solid support. A disadvantage of this approach is the lack of correlating structure with function in screening the modified peptides, as well as limited therapeutic application when small peptides are insufficient to mimic activity of a protein or protein complex.

While each of the technologies described above afford a large number of compounds, the usefulness of these systems for the effective rapid discovery of drug candidates is limited since all of them result in the identification of relatively small peptide ligands. In most cases, small peptides are not suited as drugs due to in vivo instability and lack of oral absorption. Furthermore, conversion of a peptide chemical lead into a pharmaceutically useful, orally active, non-peptide drug candidate is more difficult than identifying the original peptide lead since no general solution yet exists for designing effective peptide mimics.

Another significant limitation of the various approaches described above are the size and complexity of the libraries, whether they are generated as single compounds (active compound identified by it's physical location) or mixtures (active compound identified by it's tag for encoded libraries or through deconvolution, where an active compound is identified by iterative synthesis and screening of mixtures). In addition, the construction of random synthetic, native, and phage libraries have proven useful but fall short of providing a more rational approach in development of compound libraries for the identification of a novel lead chemical structure. Accordingly, there exists a need to develop new libraries comprising functionally diverse compounds to improve the drug discovery process.

RELEVANT LITERATURE

Peptide libraries constructed by chemical synthesis have been disclosed by Hogan et al., (WO 94/01102). Dawson et al. (*Science* (1994) 266:776–779) and Kent et al. (WO 96/34878) disclose a method for the chemical synthesis of proteins by native chemical ligation. Various combinations of solid and solution phase ligation technologies for the synthesis of chemokines and analogues also have been disclosed (Siani et al., IBC 3rd Annual International Conference: Chemokines, September 1996; Siani et al., NMHCC, Chemokines and Host-Cell Interaction Conference, January 1997, Baltimore, Md.; Siani et al., Peptide Symposium, Nashville, June 1997; Canne et al., American Peptide Symposium, Nashville, June 1997; and Siani, et al., *American Peptide*, Jun. 15–19, 1997, Nashville, Tenn.). Wernette-Hammond et al. (*J. Biol. Chem.* (1996) 271:8228–8235) disclose recombinant expression of chimeric proteins comprising segments from IL-8 and GRO-gamma.

SUMMARY OF THE INVENTION

Novel proteins comprising a combination of two or more functional modules from two or more different parent proteins, and libraries comprising the proteins are provided. The proteins and libraries of the invention are produced by cross-over synthesis of functional protein modules identified among a class or family of proteins. Libraries comprising novel cross-over chemokines are exemplified. The present invention includes novel therapeutic leads and compounds for characterizing the chemical basis of known ligand/ligate interactions including epitope mapping, receptor localization and isolation. The methods of the invention are applicable to other families of proteins in addition to the chemokines for diversity generation of libraries and pharmaceutical leads.

The cross-over protein libraries of the invention permit refinement of specific properties of particular protein molecules, including activity, stability, specificity and immunogenicity. The process begins with the generation of a focused set of candidate protein analogues based on a protein family identified as having functional modules. The functional protein modules can be identified by any number of means including identification of structure and function relationships. Structural relationships are preferably based on homology comparisons between nucleotide, amino acid, and/or three-dimensional analysis. The structural components can be assessed separately or in combination with functional analysis including assays which correlate structural data with a particular activity. The cross-over proteins of the invention are then prepared by ligation of the functional modules to form a single polypeptide chain. A preferred method of modular protein synthesis employs chemical ligation to join together large peptide segments to form functional polypeptides or proteins. A combination of peptide synthesis and one or more ligation steps also can be used. Solid phase and native chemical ligation techniques are preferred for constructing the cross-over proteins.

The modular protein synthesis approach permits an efficient and high-yield method for the construction of synthetic protein libraries of hybrid molecules that can be much larger than is possible with conventional synthesis techniques. After functional selection, protein molecules with desired characteristics are identified and then used as leads for subsequent cycles of synthesis and screening. The speed of modular chemical synthesis and the efficiency of the analogue identification methods enable multiple rounds of refinement to produce finely-tuned protein therapeutic candidates. Additionally, chemical ligation permits unprecedented access to extremely pure cross-over protein libraries free of cellular contaminants.

BRIEF DESCRIPTION OF THE FIGURES

FIG. 3 shows chemokine amino acid sequence patterns for RANTES, SDF-1α and MPBV.

DEFINITIONS

Figure 1:
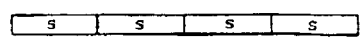
FIG. 1 shows a general method for generating molecular diversity by cross-over synthesis of CXC and CC chemokines.
Figure 1:
Figure 1:
Figure 1:

"Peptide." Two or more amino acids operatively joined by a peptide bond. By operatively joined it is intended that the structure and function of a peptide bond in a naturally occurring protein is represented.

"Protein." Two or more peptides operatively joined by a peptide bond. The term protein is interchangeable with the term polypeptide.

"Functional Protein Module." A segment of a protein comprising a sequence of amino acids that provides a particular functionality in a folded protein. The functionality is based on positioning of the sequence in three-dimensional space and can be formed by two or more discontinuous protein sequences.

"Modular Protein." A protein comprising a combination of two or more functional protein modules operatively joined by one or more peptide bonds.

"Modular Protein Library." A collection of modular protein compounds.

"Cross-Over Protein." A hybrid protein comprising one or more functional protein modules derived from different parent protein molecules. The functional protein modules are provided by two or more peptide segments joined by a native or non-native peptide bond. The segments can comprise native amide bonds or any of the known unnatural peptide backbones or a mixture thereof. May include the 20 genetically coded amino acids, rare or unusual amino acids that are found in nature, and any of the non-naturally occurring and modified amino acids.

"Cross-Over Protein Library." A collection of cross-over protein compounds.

DETAILED DESCRIPTION OF THE INVENTION

The present invention provides cross-over proteins produced by chemical ligation of two or more functional protein modules derived from two or more different parent protein molecules. The chemical ligation involves ligating under chemoselective chemical ligation conditions at least one N-terminal peptide segment comprising a functional protein module of a first parent protein and at least one C-terminal peptide segment comprising a functional protein module of a second parent protein, where the N-terminal and C-terminal peptide segments provide compatible reactive groups capable of chemoselective chemical ligation. The first and second parent proteins preferably are members of the same family of proteins, and may include one or more mutations relative to a naturally occurring parent protein molecule.

The cross-over proteins and methods of the invention provide unprecedented access to new proteins molecules useful for multiple diagnostic and drug discovery applications. For example, proteins act on receptors to elicit a characteristic biological response. Proteins are composed of functional modules that have functionality relative to the folded protein. Accordingly, cross-over ligation of two or more different functional modules from different proteins of a class or family generates new hybrid protein molecules. The cross-over proteins of the invention have unique properties that can be used to evaluate function and tune desired properties, such as biological activity as well as physicochemical properties related to formulation and administration.

The cross-over proteins of the invention also may include one or more modified amino acids, such as an amino acid comprising a chemical tag. The chemical tag may be introduced during and/or after synthesis of the cross-over protein molecule. The chemical tag may be utilized for multiple purposes such as part of the synthesis process, purification, anchoring to a support matrix, detection and the like. Of particular interest is a chemical tag provided by an unnatural amino acid comprising a chromophore. This includes a chromophore that is an acceptor and/or donor moiety of an acceptor-donor resonance energy transfer pair.

The present invention also provides libraries of cross-over proteins. A collection of cross-over proteins derived from a particular class or family of protein molecules represents a focused and rationally designed library of novel and structurally diverse cross-over protein molecules that permit collective analysis and identification of therapeutic leads that can combine properties contributed by two or more distinct parent proteins. A preferred cross-over protein library of the invention contains at least four or more unique cross-over proteins.

Libraries of cross-over proteins of the invention are prepared by ligation of distinct functional modules from a particular class or family of proteins. The functional modules may be identified by comparing nucleotide and/or amino acid sequence information of a target protein to identify one or more modules representing a particular functionality for the protein family. Computer analysis, simulation and atomic coordinate information also may be employed for comparison. As biological macromolecules (receptor, enzyme, antibody, etc.) recognize binding substrates through a number of precise physicochemical interactions, these interactions can be divided into a number of different parameters or dimensions such as size, hydrogen bonding ability, hydrophobic interactions, etc., each of which contribute to the activity of a functional protein module. Functional modules from different proteins having distinct biological activity within the family are selected to maintain the basic three-dimensional scaffold of the initial class of target molecule. The cross-over protein libraries are therefore designed to orient groups responsible for binding interactions at unique locations in three-dimensional space relative to a rudimentary protein scaffold. This allows for facile introduction of two or more functional groups in a large number of spatial arrangements. A large number of compounds prepared around each scaffold will reflect a diverse range of unique activities, sizes, shapes, and volumes.

Additional diversity can be added to the library through subsequent chemical modification of the proteins, such as amino and/or carboxyl terminal modification, and/or the incorporation of non-natural amino acids. Another example includes synthesis of functional modules of defined structure and length, where specified positions or a defined number of positions contain a random mixture of amino acids.

A double combinatorial approach also can be used in which functional groups, representing various physicochemical interacting properties, are introduced by combining functional protein modules into the scaffold building block. A second scaffold building block can be added followed by an additional round of functional group introduction. The final target molecule is prepared for screening. This approach permits the rapid production of a second or sub-library of highly functionalized target molecules from the first library, which may represent only a small collection of functional protein modules.

The cross-over proteins of the invention are generated by chemical ligation techniques. The chemical ligation method of the invention involves cross-over chemoselective chemical ligation of (i) at least one functional N-terminal peptide segment comprising one or more functional protein modules derived from a first parent protein, and (ii) at least one functional C-terminal peptide segment comprising one or more functional protein modules derived from a second parent protein having one or more properties and an amino acid sequence that is different from the first parent protein under chemoselective chemical ligation conditions, where the N-terminal peptide segment and the C-terminal peptide segment provide compatible reactive groups capable of chemoselective chemical ligation. The cross-over ligation reaction is allowed to proceed under conditions whereby a covalent bond is formed between the N-terminal and C-terminal peptide segments so as to produce a chemical ligation product comprising a cross-over protein.

Figure 2:
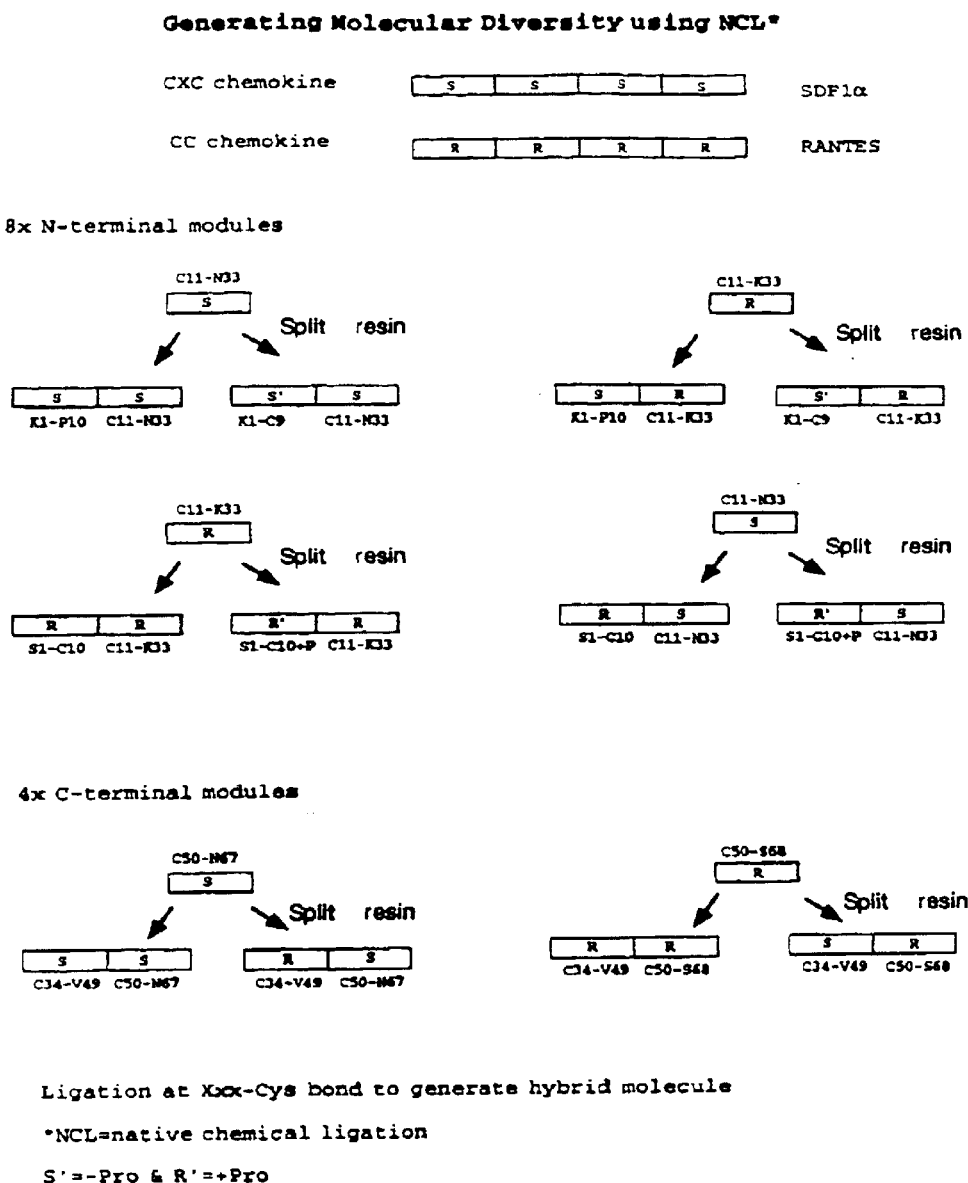
FIG. 2 shows a method for generating molecular diversity by cross-over synthesis of the CXC chemokine SDF-1α and the CC chemokine RANTES.

A peptide segment utilized for construction of a cross-over protein of the invention contains an N-terminus and a C-terminus with respect to directionality of the amino acid sequence comprising the segment. For a given chemical ligation event, two protein segments, each comprising one or more functional protein modules, form a covalent bond between a reactive group donated by an amino acid of the N-terminal end of the first segment and a reactive group donated by an amino acid of the C-terminal end of the second segment (i.e., head to tail chemical ligation). Thus use of the terminology "N-terminal peptide segment" and "C-terminal peptide segment" refers to the directionality of the protein segment relative to a particular chemoselective ligation event and/or the final cross-over protein product. By way of example, and with reference to FIGS. 1–2 illustrating cross-over ligation of the CXC and CC chemokines SDF1α (S) and RANTES (R), respectively, a given cross-over chemokine exemplified in FIGS. 1–2 may be formed by chemical ligation utilizing protein or peptide segments that comprise one or more functional modules (S, S', R and R'), such as two peptide segments (e.g., ligation of SS' (N-terminal) and RR' (C-terminal) to yield SS'RR' cross-over chemokine), three peptide segments (e.g., ligation of S (N-terminal) and S'R (C-terminal) to yield SS'R (N-terminal), followed by ligation of SS'R (N-terminal) to R' (C-terminal) to yield SS'RR' cross-over protein), or four peptide segments (e.g., ligation of S (N-terminal) and S' (C-terminal) to yield SS' (N-terminal), and ligation of R (N-terminal) and R' (C-terminal) to yield RR' (C-terminal), followed by ligation of SS' (N-terminal) and RR' (C-terminal) to yield SS'RR' cross-over chemokine). As can be appreciated, any number of modular combinations and ligation orders are possible.

The cross-over ligations may be performed in single or separate reactions, and optionally include a plurality of chemoselective ligation compatible N- and C-terminal peptide segments representing a mixture of functional protein modules derived from two or more different parent proteins, so as to obtain a plurality of unique cross-over proteins. When a mixture of unique N-terminal and C-terminal peptide segments are employed, the ligated products can be identified and separated from non-specific side reactions and unligated components by any number of separation techniques, such affinity or high performance liquid chromatography. Further deconvolution can be utilized to pool or separate the desired ligation products. Also, the mixtures may represent specific groups or sub-groups of peptide segments so as to regulate the number of possible desired ligation outcomes per reaction. One or more internal controls (e.g., parent protein molecules), or coding tags (e.g., chemically tagged cross-over ligation peptide segments) may be included to ease deconvolution. Activity screens also may be used in conjunction with deconvolution.

In a preferred embodiment, one or more of the N-terminal and C-terminal peptide segments utilized in a given cross-over chemical ligation are pre-formed by cross-over ligation, which are then employed for construction of cross-over proteins. This aspect of the invention involves cross-over ligation of two or more functional protein modules derived from different parent proteins of the same family by (i) generating a plurality of functional N-terminal peptide segments having one or more functional protein modules obtained by cross-over ligation of two or more different parent protein molecules, and a plurality of functional C-terminal peptide segments having one or more functional protein modules obtained by cross-over ligation of two or more different parent protein molecules, followed by (ii) cross-over ligation of the plurality of cross-over N-terminal and C-terminal modules so as to obtain a plurality of unique cross-over proteins.

One of ordinary skill in the art will recognize that the larger the library of unique cross-over proteins, the greater the diversity and information and leads derivable therefrom. The size and diversity of a library can be determined by calculating the number of possible unique cross-over events based on the number of unique N-terminal and C-terminal modules as described above. This may employ simulations, modeling and the like as a basis for designing cross-over proteins of the invention, followed by synthesis and screening of the cross-over molecules for activity. It also will be appreciated by one of ordinary skill that molecules exhibiting activity, a range of activity or no activity for a given screening assay provide useful structure-activity relationship (SAR) and quantitative SAR (QSAR) information for characterizing structure-function of individual modules and combinations of modules, and thus iterative design, screening and synthesis. For instance, libraries can be generated by computer simulation (virtual library) followed by synthesis employing the combinatorial ligation chemistry approaches of the invention (physical library). The physical libraries then can be screened in a biological assay and resulting activity profiles assessed relative to a given functionality imparted, modified or otherwise removed and the like by a module or combination of modules.

The cross-over proteins can be made to resemble or duplicate features of naturally occurring peptides or segments of naturally occurring proteins. The design of a particular cross-over protein is based on its intended use and on considerations of the method of synthesis. As the proteins increase in length, they have a greater tendency to adopt elements of secondary structure such as loops, α-helicies and β-sheet structures connected by discrete turns, which impart an overall decrease in flexibility. These elements in part are the components which comprise a scaffold that present functional groups responsible for specific biological activity. From knowledge of the features that contribute to these structures, the proteins can be specifically designed to contain them. Of particular interest are cross-over protein molecules synthesized by combining a functional module from a first protein with a functional module from a second protein. Additional functional modules can be combined from the same and/or one or more other proteins. A preferred cross-over protein is produced by combining one or more functional modules from a first chemokine and a second chemokine. The cross-over protein molecules are assayed for biological activity, for example, the cross-over chemokines are evaluated for induction of lyphocyte chemotaxis and binding to receptors.

The cross-over proteins can be linear, cyclic or branched, and often composed of, but not limited to, the 20 genetically encoded L-amino acids. A chemical synthetic approach permits incorporation of novel or unusual chemical moieties including D-amino acids, other unnatural amino acids, ester or alkyl backbone bonds in place of the normal amide bond, N- or C-alkyl subtituents, side chain modifications, and constraints such as disulfide bridges and side chain amide or ester linkages. The chemical modification is designed to impart changes in biological potency, stability related to halflife in vivo and storage, and the ability to interact with or covalently label a biological macromolecule receptor for localization of structure-function assays.

Peptide segments utilized for initial ligation and synthesis of the cross-over proteins of the invention may be synthesized chemically, ribosomally in a cell free system, ribosomally within a cell, or any combination thereof. Accordingly, cross-over proteins generated by ligation according to the method of the invention include totally synthetic and semi-synthetic cross-over proteins. Ribosomal synthesis may employ any number of recombinant DNA and expression techniques, which techniques are well known. See, for example, Sambrook et al. (1989, "Molecular Cloning, A Laboratory Manual," Cold Springs Harbor Press, New York); "Recombinant Gene Expression Protocols," Humana Press, 1996; and Ausubel et al. (1989, "Current Protocols in Molecular Biology," Green Publishing Associates and Wiley Interscience, New York). For chemical synthesis, peptide segments can be synthesized either in solution, solid phase or a combination of these methods following standard protocols. See, for example, Wilken et al. (*Curr. Opin. Biotech.* (1998) 9(4):412–426), which reviews chemical protein synthesis techniques. The solution and solid phase synthesis methods are readily automated. A variety of peptide synthesizers are commercially available for batchwise and continuous flow operations as well as for the synthesis of multiple peptides within the same run. The solid phase method consists basically of anchoring the growing peptide chain to an insoluble support or resin. This is accomplished through the use of a chemical handle, which links the support to the first amino acid at the carboxyl terminus of the peptide. Subsequent amino acids are then added in a stepwise fashion one at a time until the peptide segment is fully constructed. Solid phase chemistry has the advantage of permitting removal of excess reagents and soluble reaction by products by filtration and washing. The protecting groups of the fully assembled resin bound peptide chain are removed by standard chemistries suitable for this purpose. Standard chemistries also may be employed to remove the peptide chain from the resin. Cleavable linkers can be employed for this purpose. For solution phase peptide synthesis this generally involves reacting individual protected amino acids in solution to generate protected dipeptide product. After removal of a protection group to expose a reactive group for addition of the next amino acid, a second protected amino acid is reacted to this group to give a protected tripeptide. The process of deprotection/amino acid addition is repeated in a stepwise fashion to yield a protected peptide product. One or more to these protected peptides can be reacted to give the full-length protected peptide. Most or all or the remaining protecting groups are removed to generate an unprotected synthetic peptide segment. Thus, solid phase or solution phase chemistries may be employed to form synthetic peptides comprising one or more functional protein modules.

The preferred method of synthesis employs a combination of chemical synthesis and chemical ligation techniques. By way of example, chemical synthesis approaches described above may be utilized in combination with various chemoselective chemical ligation techniques for producing the cross-over proteins of the invention. Chemoselective chemical ligation chemistries that can be utilized in the methods of the invention include native chemical ligation (Dawson et al., *Science* (1994) 266:77–779; Kent et al., WO 96/34878), extended general chemical ligation (Kent et al., WO 98/28434), oxime-forming chemical ligation (Rose et al., *J. Amer. Chem. Soc.* (1994) 116:30–33), thioester forming ligation (Schnolzer et al., *Science* (1992) 256:221–225), thioether forming ligation (Englebretsen et al., *Tet. Letts.* (1995) 36(48):8871–8874), hydrazone forming ligation (Gaertner et al., *Bioconj. Chem.* (1994) 5(4):333–338). thaizolidine forming ligation and oxazolidine forming ligation (Zhang et al., *Proc. Natl. Acad. Sci.* (1998) 95(16):9184–9189; Tam et al., WO 95/00846). The preferred chemical ligation chemistry for synthesis of cross-over proteins according to the method of the invention is native chemical ligation.

For example, the synthesis of proteins by native chemical ligation is disclosed in Kent et al., WO 96/34878. In general, a first oligopeptide containing a C-terminal thioester is reacted with a second oligopeptide with an N-terminal cysteine having an unoxidized sulfhydryl side chain. The unoxidized sulfhydryl side chain of the N-terminal cysteine is condensed with the C-terminal thioester in the presence of a catalytic amount of a thiol, preferably benzyl mercaptan, thiophenol, 2-nitrothiophenol, 2-thiobenzoic acid, 2-thiopyridine, and the like. An intermediate oligopeptide is produced by linking the first and second oligopeptides via a β-aminothioester bond, which rearranges to produce an oligopeptide product comprising the first and second oligopeptides linked by an amide bond.

Synthesis of cross-over proteins according to the methods of the invention by a combination of chemical ligation and chemical synthesis permits facile incorporation of one or more chemical tags. These include synthesis and purification handles, as well as detectable labels and optionally chemical moieties for attaching the cross-over protein to a support matrix for screening and diagnostic assays and the like. As can be appreciated, in some instances it may be advantageous to utilize a given chemical tag for more than one purpose, e.g., both as a handle for attaching to support matrix and as a detectable label. Examples of chemical tags include metal binding tags (e.g., his-tags), carbohydrate/substrate binding tags (e.g., cellulose and chitin binding domains), antibodies and antibody fragment tags, isotopic labels, haptens such as biotin and various unnatural amino acids comprising a chromophore. A chemical tag also may include a cleavable linker so as to permit separation of the cross-over protein from the chemical tag depending on its intended end use.

For example, it may be convenient to conjugate a fluorophore to the N-terminus of a resin-bound peptide utilized for synthesis and ligation of cross-over proteins of the invention before removal of other protecting groups and release of the labeled peptide from the resin. About five equivalents of an amine-reactive fluorophore are usually used per amine of the immobilized peptide. Fluorescein, eosin, Oregon Green, Rhodamine Green, Rhodol Green, tetramethylrhodamine, Rhodamine Red, Texas Red, coumarin and NBD fluorophores, the dabcyl chromophore and biotin are all reasonably stable to hydrogen fluoride (HF), as well as to most other acids. (Peled et al., *Biochemistry* (1994) 33:7211; Ben-Efraim et al., *Biochemistry* (1994) 33:6966). With the possible exception of the coumarins, these fluorophores are also stable to reagents used for deprotection of peptides synthesized using FMOC chemistry (Strahilevitz et al., *Biochemistry* (1994) 33:10951). The t-BOC and α-FMOC derivatives of ε-dabcyl-L-lysine also can be used to incorporate the dabcyl chromophore at selected sites in a polypeptide sequence. The dabcyl chromophore has broad visible absorption and can used as a quenching group. The dabcyl group also can be incorporated at the N-terminus by using dabcyl succinimidyl ester (Maggiora et al, supra). EDANS is a common fluorophore for pairing with the dabcyl quencher in fluorescence resonance energy transfer experiments. This fluorophore is conveniently introduced during automated synthesis of peptides by using 5-((2-(t-BOC)-γ-glutamylaminoethyl) amino) naphthalene-1-sulfonic acid (Maggiora et al., *J Med Chem* (1992) 35:3727). An α-(t-BOC)-ε-dansyl-L-lysine can be used for incorporation of the dansyl fluorophore into polypeptides during synthesis (Gauthier, et al., *Arch Biochem Biophys* (1993) 306:304). Like EDANS, its fluorescence overlaps the absorption of dabcyl. Site-specific biotinylation of peptides can be achieved using the t-BOC-protected derivative of biocytin (Geahlen et al., *Anal Biochem* (1992) 202:68). The racemic benzophenone phenylalanine analog can be incorporated into peptides following its t-BOC or FMOC protection (Jiang, et al., *Intl J Peptide Prot. Res* (1995) 45:106). Resolution of the diastereomers is usually accomplished during HPLC purification of the products; the unprotected benzophenone can also be resolved by standard techniques in the art. Keto-bearing amino acids for oxime coupling, aza/hydroxy tryptophan, biotyl-lysine and D-amino acids are among other examples of unnatural amino acids that can be utilized. It will be recognized that other protected amino acids for automated peptide synthesis can be prepared by custom synthesis following standard techniques in the art.

A chemical tag also can be introduced by chemical modification using a reactive substance that forms a covalent linkage once having bound to a reactive group of the target cross-over protein molecule and/or one or more module containing peptide segments used to construct the protein. For example, a target cross-over protein can include several reactive groups, or groups modified for reactivity, such as thiol, aldehyde, amino groups, suitable for coupling the chemical tag by chemical modification (Lundblad et al., In: Chemical Reagents for Protein Modification, CRC Press, Boca Raton, Fla., (1984)). Site-directed mutagenesis of a cross-over protein module produced ribosomally and/or via chemical synthesis also can be used to introduce and/or delete such groups from a desired position. Any number of chemical tags including biotinylation probes of a biotin-avidin or strepavidin system, antibodies, antibody fragments, carbohydrate binding domains, chromophores including fluorophores and other dyes, lectin, nucleic acid hybridization probes, drugs, toxins and the like, can be coupled in this manner. For instance, a low molecular weight hapten, such a fluorophore, digoxigenin, dinitrophenyl (DNP) or biotin, can be chemically attached to a target reactive group by employing haptenylation and biotinylation reagents. The haptenylated polypeptide then can be directly detected using fluorescence spectroscopy, mass spectrometry and the like, or indirectly using a labeled reagent that selectively binds to the hapten as a secondary detection reagent. Commonly used secondary detection reagents include antibodies, antibody fragments, avidins and streptavidins labeled with a fluorescent dye or other detectable marker.

Depending on the reactive group, chemical modification can be reversible or irreversible. A common reactive group targeted in proteins are thiol groups, which can be chemically modified by haloacetyl and maleimide labeling reagents that lead to irreversible modifications and thus produce more stable products. For instance, reactions of sulfhydryl groups with α-haloketones, amides, and acids in the physiological pH range (pH 6.5–8.0) are well known and allow for the specific modification of cysteines in peptides and polypeptides (Hermason et al., In: Bioconjigate Techniques, Academic Press, San Diego, Calif., pp 98–100, (1996)). Covalent linkage of a detectable label also can be triggered by a change in conditions, for example, in photoaffinity labeling as a result of illumination by light of an appropriate wavelength. For photoaffinity labeling, the label, which is often fluorescent or radioactive, contains a group that becomes chemically reactive when illuminated (usually with ultraviolet light) and forms a covalent linkage with an appropriate group on the molecule to be labeled. An important class of photoreactive groups suitable for this purpose is the aryl azides, which form short-lived but highly reactive nitrenes when illuminated. Flash photolysis of photoactivatable or "caged" amino acids also can be used for labeling peptides that are biologically inactive until they are photolyzed with UV light. Different caging reagents can be used to modify the amino acids, such derivatives of o-nitrobenzylic compounds, and detected following standard techniques in the art. (Kao et al., "Optical Microscopy: Emerging Methods and Applications," B. Herman, J. J. Lemasters, eds., pp. 27–85 (1993)). The nitrobenzyl group can be synthetically incorporated into the biologically active molecule via an ether, thioether, ester (including phosphate ester), amine or similar linkage to a hetero atom (usually O, S or N). Caged fluorophores can be used for photoactivation of fluorescence (PAF) experiments, which are analogous to fluorescence recovery after photobleaching (FRAP). Those caged on the ε-amino group of lysine, the phenol of tyrosine, the γ-carboxylic acid of glutamic acid or the thiol of cysteine can be used for the specific incorporation of caged amino acids in the sequence. Alanine, glycine, leucine, isoleucine, methionine, phenylalanine, tryptophan and valine that are caged on the α-amine also can be used to prepare peptides that are caged on the N-terminus or caged intermediates that can be selectively photolyzed to yield the active amino acid either in a polymer or in solution. (Patchornik et al., *J Am Chem Soc* (1970) 92:6333). Spin labeling techniques of introducing a grouping with an unpaired electron to act as an electron spin resonance (ESR) reporter species may also be used, such as a nitroxide compound (—N—O) in which the nitrogen forms part of a sterically hindered ring (Oh et al., *Science* (1996) 273:810–812).

Selection of a chemical tag for a given cross-over protein generally depends on its intended use. In particular, the chemical ligation methods and compositions of the invention can utilize a chemical tag for application in a screening assay of the invention characterized by binding of a cross-over protein to a target receptor. These include diagnostic assays, screening new compounds for drug development, and other structural and functional assays that employ binding of a cross-over protein to a target receptor. The methods include the steps of contacting a receptor with one or more cross-over proteins obtained from a cross-over protein library, and identifying a cross-over protein from the library that is a ligand for the receptor in an assay characterized by detection of binding of the ligand to the receptor. The methods preferably employ one or more of cross-over proteins having a detectable label, such as an unnatural amino acid including a chromophore. Of particular interest are chromophores comprising an acceptor and/or donor moiety of an acceptor-donor resonance energy transfer pair. For cross-over proteins comprising at least one chromophore, a preferred form of detection is fluorescence detection. When a resonance energy transfer pair is represented, a preferred form of fluorescence detection is fluorescence resonance energy transfer detection (FRET). Screening methods of particular interest involve contacting a target receptor with a cross-over protein ligand, where at least the cross-over ligand is labeled with one or more chromophores, followed by detection of ligand binding by fluorescence spectroscopy. The methods, compounds and compositions of the invention are readily adaptable to high throughput screening.

When employed in a screening or diagnostic assay, a chemical tag can be utilized as a handle to attach a cross-over protein of the invention to a support matrix. Various reversible binding, covalent attachment, and/or cleavable linker moieties may be used for this purpose to tether the molecule of interest to the support matrix. A preferred support matrix is one amenable to storage, shipping, multi-plex screening and/or automated applications, such as chromatography columns, beads, multi-sample sheets such as nitrocellulose sheets, multi-well plates and the like. In a preferred embodiment, the cross-over proteins are attached to a solid support matrix in a spatially addressable array. For instance, a set of cross-over proteins representing a desired cross-over ligation structure or group of structures may be logically arranged in spatially addressable multi-well micro-titer plates (e.g., 96 and/or 386 well microtiter plates) with a one or more cross-over proteins per well. These arrays may be assembled into larger array sets to increase information derivable from a screening and/or diagnostic assay.

Assays of particular interest employ receptors provided by tissues or cell preparations, synthetic preparations and the like. Receptors of particular interest are lipid membrane-bound receptors generated by lipid matrix-assisted chemoselective chemical ligation as described in U.S. patent application Ser. No. 09/144,964. Screening for binding of a cross-over protein ligand comprising one or more chromophores to a target receptor is preferably performed in a FRET assay. Ligand binding can be measured by any number of methods known in the art for FRET analyses, including steady state and time-resolved fluorescence by monitoring the change in fluorescence intensity, emission energy and/or anisotropy, for example, through energy transfer from a donor moiety to an acceptor moiety of the FRET system. (See, e.g., Wu et al., Analytical Biochem. (1994) 218: 1–13). FRET assays allow not only distance measurements, but also resolution of the range of donor-to-acceptor distances. FRET also can be used to show that the ligand and/or target receptor exists alternately in a single conformational state, or with a range of donor-to-acceptor distances when in a different state, such as when bound to a ligand. More than one donor-acceptor pairing may also be included.

For FRET assays, the cross-over protein ligand is designed to contain at least one chromophore of a donor-acceptor system. The donor molecule is always a fluorescent (or luminescent) one for detection. The acceptor molecule can be either fluorescent or non-fluorescent. Thus for a donor-acceptor system, at least two chromophores are provided: the first is provided by the cross-over ligand; the second can be provided by the receptor, a matrix to which the receptor and/or ligand is attached and/or embedded such as a lipid membrane, or by one or more of a second ligand for the receptor and/or cross-over ligand.

When choosing a chromophore donor-acceptor pair for FRET, positioning of the first chromophore in a target cross-over protein ligand is selected to be within a sufficient distance of a second chromophore to create a donor-acceptor fluorescence resonance energy transfer system. For instance, energy transferred from the donor to an acceptor involves coupling of dipoles in which the energy is transferred over a characteristic distance called the Forster radius ($R_o$), which is defined as the distance at which energy transfer efficiency is 50% (i.e., distance at which 50% of excited donors are deactivated by FRET). These distances range from about 10 to 100 Angstroms (Å), which is comparable to the diameter of many proteins and comparable to the thickness of membranes. Intrinsic tryptophan or tyrosine sometimes may be used as chromophores in distance measurements, but in most cases the Forster distance is limited to above 30 Å. However, an acceptor molecule comprising clusters of acceptors with high molar absorption coefficient for each acceptor may achieve a further extension of Forster distance. Thus average distances over 100 Å can be measured. As the Forster distances can be reliably calculated from the absorption spectrum of the acceptor and the emission spectrum of the donor, FRET allows determination of molecular distances. Once the Forster distance is known, the extent of energy transfer can be used to calculate the donor-to-acceptor distance.

Donor-acceptor chromophores applicable for biological molecules, and for which Forster distances are known when paired, include but are not limited to the following chromophores: ANAI (2-anthracene N-acetylimidazole); BPE (B-phycoerythrin); CF (caboxyfluorescein succinimidyl ester); CPM (7-diethylamino-3-(4'-maleimidylphenyl)-4-methylcoumarin); CY5 (carboxymethylindocyanine-N-hydroxysuccinimidyl ester, diI-$C_{13}$, 1,1'-dioctadecyl-3,3,3', 3'-tetramethyl-indocarbocyanine; diO-$C_{14}$, 3,3'-ditetradecyloxacarbocyanine); DABM (4-dimethylamino-phenylazo-phenyl-4'-maleimide); DACM ((7-(dimethylamino)coumarin-4-yl)-acetyl); DANZ (dansylaziridine); DDPM (N-(4-dimethylamino-3,5-dinitrophenyl)maleimide); DMAMS (dimethylamino-4-maleimidostilbene); DMSM (N-(2,5-dimethoxystiben-4-yl)-maleimide); DNP (2,4-dinitrophneyl); -A (1,$N^6$-ethenoadenosine); EIA (5-(iodoacetetamido)eosin); EITC (eosin thiosemicarbazide); $F_2$DNB (1,5-difluro-2,4'-dinitrobenzene); $F_2$DPS (4,4'-difluoro-3,3'-dinitrophenylsulfone); FITC (fluorescein-5-isothiocyanate); FM (fluorescein-5-maleimide); FMA (fluorescein mercuric acetate); FNAI (fluorescein N-acetylimidazole); FTS (fluorescein thiosemicarbazide); IAANS (2-(4'-iodoacetamido)aniino)naphthalene-6-sulfonic acid); IAEDANS (5-(2-((iodoacetyl)amino)ethyl)amino)-naphthlene-1-sulfoni acid); IAF (5-iodoacetamido-fluorescein); IANBD (N-((2-(iodoacetoxy)ethyl)-N-methyl) amino-7-nitrobenz-2-oxa-1,3-diazole); IPM (3(4-isothiocyanatophenyl)7-diethyl-4-amino-4-methylcoumarin); ISA (4-(iodoacetamido)salicylic acid); LRH (lissaminerhodamine); LY (Lucifer yellow); mBBR (monobromobimane); MNA ((2-methoxy-1-naphthyl)-methyl); NAA (2-naphthoxyacetic acid); NBD (7-nitro-2,1, 3-benzoxadiazol-4-yl); NCP (N-cyclohexyl-N'-(1-pyrenyl) carbodiimide); ODR (octadecylrhodamine); PM (N-(1-pyrene)-maleimide); SRH (sulforhodamine); TMR (tetramethylrhodamine); TNP (trinitrophenyl); TR (Texas red); BODIPY ((N1-B)-N1'-(difluoroboryl)-3,5'-dimethyl-2-2'-pyrromethene-5-propionic acid, N-succinimidyl ester); and lanthanide-ion-chelates such as an iodoacetamide derivative of the Eu3+-chelate of N-(p-benzoic acid) diethylenetriamine-N,N',N'-tetraacetic acid (DTTA).

Since energy transfer measurement is most sensitive to distance variation when donor-acceptor separation is close to their Forster distance, the molecule comprising the first chromophore of a donor-acceptor pair system is selected or engineered so that the first and second chromophores approach or are at the Forster distance. Table 1 shows some typical Forster distances of donor-acceptor pairs.

TABLE 1

| Donor | Acceptor | Forster Distance (Å) |
|---|---|---|
| Fluorescein | Tetramethylrhodamine | 55 |
| IAEDANS | Fluorescein | 46 |
| EDANS | DABCYL | 33 |
| Fluorescein | Fluorescein | 44 |
| BODIPY FL | BODIPY FL | 57 |

Extensive compilations of Forster distances for various donor-acceptor pairs and their specific applications in FRET analysis of biological molecules including peptides, proteins, carbohydrates and lipids are well known in the art. (See, e.g., Wu et al., supra; Berlman et al., (1973) Energy Transfer Parameters of Aromatic Compounds, Academic Press, New York; Van der Meer et al., (1994) "Resonance Energy Transfer Theory and Data," VCH Publishers; dos Remedios et al., *J Muscle Res Cell Motility* (1987) 8:97; Fairclough et al., *Meth Enzymol* (1978) 48:347). These Forster distances are used as a general guide when selecting a particular donor-acceptor pair.

In addition to selecting donor and acceptor moieties that are in close proximity (typically 10–100 Å) and approach or are at the Forster distance, the FRET chromophore pairs are selected so that the absorption spectrum of the acceptor overlaps the fluorescence emission spectrum of the donor, and the donor and acceptor transition dipole orientations are approximately parallel. Moreover, for anisotropy assays the chromophores are preferably positioned so that tumbling of the donor or acceptor moiety is minimized. An advantage of reducing chromophore tumbling is increased sensitivity in FRET detection by reducing background noise in the spectrum.

For most applications, the donor and acceptor dyes are different, in which case FRET can be detected by the appearance of sensitized fluorescence of the acceptor (acceptor enhancement), by quenching of donor fluorescence (donor quenching), or fluorescence polarization (anisotropy). When the donor and acceptor are the same, FRET is typically detected by anisotropy. For instance, donor quenching (quenching of fluorescence) can be used to detect energy transfer. Excitation is set at the wavelength of donor absorption and the emission of donor is monitored. The emission wavelength of donor is selected such that no contribution from acceptor fluorescence is observed. The presence of acceptor quenches donor fluorescence. A wide variety of small molecules or ions act as quenchers of fluorescence, that is, they decrease the intensity of the emission. These substances include iodide, oxygen, chlorinated hydrocarbons, amines, and disulfide groups. The accessibility of fluorophores to quenchers is widely used to determine the location of probes on macromolecules, or the porosity of cross-over proteins or target receptor to the quenchers.

Acceptor enhancement detection techniques can be used when an acceptor is fluorescent, and its fluorescence intensity is enhanced when energy transfer occurs (with excitation into the donor). This provides additional methods to visualize energy from a fluorescence spectrum. In an emission spectrum, one excites at the wavelength of donor absorption and observes the intensity increase of acceptor. In an excitation spectrum, one sets detection at the acceptor emission wavelength and observes enhancements of intensity at a wavelength range where donor absorbs.

Anisotropy (or fluorescence polarization) analysis using FRET is of particular interest. The polarization properties of light and the dependence of light absorption on the alignment of the fluorophores with the electric vector of the incident light provide the physical basis for anisotropic measurements. Fluorescence probes usually remain in the excited state from 1 to 100 nanoseconds (ns), a duration called the fluorescence lifetime. Because rotational diffusion of proteins also occurs in 1–100 ns, fluorescence lifetimes are a favorable time scale for studies of the associative and/or rotational behavior of macromolecules. Other probes may be employed that remain in the excite state longer than 1–100 ns, such as those that remain in excited state for several 100 $\mu$s. When a sample of a cross-over protein system comprising an appropriate donor-acceptor chromophore pair is illuminated with vertically polarized light, the emission can be polarized. When energy transfer occurs between the same molecules in identical environments, fluorescence intensity or lifetime does not change. The anisotropy on the other hand may change due to likely change in chromophore orientation. For example, binding of cross-over protein ligand may alter the rotational motions of a receptor for the ligand during the lifetime of the excited state, where slower rotational diffusion results in higher polarization of the emitted light. Hence, if a receptor binds a ligand that induces a conformational change in the chromophore orientation by decreasing its rotational rate, the anisotropy increases. Thus, by means of fluorescence, and in particular, measurements of fluorescence polarization (or anisotropy), it is possible to measure rotational motions of a cross-over protein ligand and/or receptor for the ligand.

Homogenity and structural identity of the desired covalent ligation product can be confirmed by any number of means including high performance liquid chromatography (HPLC) using either reverse phase or ion exchange columns, mass spectrometry, crystallography and nuclear magnetic resonance (NMR). Characterization of synthetic peptides also can be performed by a combination of amino acid analysis and mass spectrometry. The positions of the modifications and deletions, if present, can be identified by sequencing with either chemical methods (Edman chemistry) or tandem mass spectrometry.

The chemical ligation approaches described herein is extendable to the combination (cross-over) of as many segments or functional modules as is possible based upon chemical ligation sites present in the sequence. For example, native chemical ligation at naturally occurring cysteine residues can be adapted to other regions devoid of cysteines by introducing cyteines at other positions. The same is true for other ligation chemistries,. i.e., chemoselective reactive groups can be engineered into a desired position so as to facilitate site-directed ligation. The chemical ligation approach is applicable to many protein systems. Combination of segments from regions of related proteins with analogous segments of related proteins is advantageous because it capitalizes on the diversity of a class of proteins, creating new proteins with new properties. These new properties may be novel (unknown in either parent protein) or more restricted (a subset of the binding properties of the parent proteins). Either of these new types of properties are desirable.

Of particular interest are classes of proteins that have therapeutic potential, and have functional modules that are readily accessible by chemical synthesis. A number of classes of proteins are known and include the chemokines; macrophage migration inhibitory factor; other cytokines; trefoil peptides; growth factors; protease inhibitors; and toxins. For example, these proteins are ligands for particular receptors.

Protein ligands of particular interest are those which are capable of binding to various receptors such as enzyme-linked receptors, fibronectin-like receptors, the seven transmembrane receptors, and the ion channel receptors, including the tryosine and serine-theronine kinases, and gluanylate cyclase families of enzyme-linked receptors. Examples of the tyrosine kinase family of receptors include epidermal growth factor, insulin, platelet-derived growth factor, and nerve growth factor. Examples of the serine kinase family of receptors include growth factor β-family. Examples of the guanylate cyclase family includes those receptors that generate cyclic GMP (cGMP) in response to atrial natriuretic factors. Examples of the seven-transmembrane receptors include those membrane proteins that bind catecholamines, histamines, prostoglandins, etc., and the opsins, vasopressin, chemokine and melanocortin receptors. Examples of the ion channel receptors are represented by the ligand- and voltage-gated channel membrane protein receptors, and include the acetylcholine activated sodium channels, glycine and gamma-aminoisobutyric acid activated chloride channels, and serotonin and glutamate activated calcium channels, and the family of cyclic nucleotide-gated channels (cAMP and cGMP), and the family of inositol 1,4,5-triphosphate (IP3) and the cyclic ADP-ribose receptors that modulate calcium storage. One of ordinary skill in the art will recognize that nucleic acid and/or amino acid sequences for the above and additional receptors and their protein ligands can be identified in various genomic and protein related databases. Examples of publicly accessible databases include as Gen-Bank (Benson et al., *Nucleic Acids Res*. (1998) 28(1):1–7, USA National Center for Biotechnology Information, National Library of Medicine, National Institutes of Health, Bethesda, Md., USA), TIGR Database (The Institute for Genomic Research, Rockville, Md., USA) Protein Data Bank (Brookhaven National Laboratory, USA), and the ExPASy and Swiss-Protein database (Swiss Institute of Bioninformatics, Geneve, Switzerland).

Of particular interest are protein classes or families of proteins amenable to native chemical ligation, and thus having naturally occurring conserved cysteine residues, or residues locations into which cysteine residues can be introduced. Examples include chemokines, agouti-related proteins, and the sex determining proteins DSX and DMT1.

Preferred cross-over proteins of the invention include ligands for the chemokine receptors and melanocortin receptors. Chemokines comprise a large family of structurally homologous cytokines, approximately 8 to 10 kD in size. These molecules share the ability to stimulate leukocyte movement (chemokinesis) and directed movement (chemotaxis). All of these molecules contain two internal disulfide loops. Chemokines have been classified into subfamilies, based on whether the two amino terminal cysteine residues are immediately adjacent (cys—cys or CC) or separated by one amino acid (cys-X-cys or CXC) or three amino acids (cys-XXX-cys or CXXXC) based on spacing proximal for the amino terminus. The chemokines fall into two major subclasses: (1) CC chemokines, which generally act on leukocytes including monocytes, T-cells, eosinophils, and basophils; and (2) CXC chemokines, which are primarily involved in acute inflammation and neutrophil activation. Members of the CXC, α-chemokine or 4 q family map to human chromosome 4 q12–21. The chemokine protein family comprises more than 65 proteins identified to date. Some of these include, members of the CXC chemokine group, such as Platelet Factor 4 (PF4), Platelet Basic Protein (PBP), Interleukin-8 (IL-8), Melanoma Growth Stimulatory Activity Protein (MGSA), Macrophage Inflammatory Protein 2 (MIP-2), Mouse Mig (m119), Chicken 9E3 (or pCEF-4), Pig Alveolar Macrophage Chemotactic Factors I and II (AMCF-I and -II), Pre-B Cell Growth Stimulating Factor (PBSF) (Stromal Cell-Derived Factor 1) (SDF-1), and IP10, a γ-interferon induced protein. Members of the CC chemokine group, or β-chemokine or 17q family map to human chromosome 17q11–32 (murine chromosome 11)., and include Monocyte Chemotactic Protein 1, 2 and 3 (MCP–1, –2.–3), Macrophage Inflammatory Protein 1 α,β, and γ (MIP-1-alpha, MIP-1-α, MIP-1-β, and MIP-1-γ Macrophage Inflammatory Proteins 3, 4 and 5 (MIP-3, MIP-4, and MIP-5), LD-78 β RANTES, Eotaxin, 1–309 (also known, in mouse, as TCA3), mouse protein C10, and mouse protein Marc/FIC. In addition to the CC and CXC families of chemokines, other groups have been identified including the "C" chemokines that are encoded by the genes SCYC1 ans SCYC2, the "CXXXC" chemokines encoded by SCYD1, and virus-encoded chemokines from viruses such as Marek's disease virus (Gallid herpesvirus 1) (Eco Q protein), stealth virus (unclassified), Kaposi's sarcoma-associated herpes-like virus (vMIP-IA) and (vMIP-I), Kaposi's sarcoma-associated herpes-like virus (vMIP-1B) and (vMIP-II), malluscum contagiosum virus (MC148R), murine cytomegalovirus (MCK-1 (ORF HJ1), human herpesvirus-6 variant A strain (EDRF3), and human herpesvirus-6 variant B strain (Z29) (CB11R).

Many of the chemokines are strongly expressed during the course of a number of pathophysiological processes including autoimmune diseases, cancer, atherosclerosis, and chronic inflammatory diseases. The biological activities of chemokines are mediated by specific receptors and also by receptors that bind several other proteins. For instance, the chemokine receptors include the CCR1, CCR2, CCR3, CCR4, CCR5, CCR6, CCR8, CXCR1, CXCR2, CXCR3, and CXCR4 chemokine receptors. Also included are the P-chemokine receptors and the unclassified chemokine receptors. There also are several receptors with homology to the chemokine receptors. For example, ligands for CCR1 include RANTES, MIP-1α, MCP-2, MCP3. Ligands for CCR2 include MCP-1, MCP-2, MCP-3, and MCP-4. Ligands for CCR3 include Eotaxin, eotaxin-2, RANTES, MCP-2, MCP-3, and MCP-4. Ligands for CCR4 include TARC, RANTES, MIP-1α, and MCP-1. Ligands for CCR5 include RANTES, MIP-1α, and MIP-1β. Ligands for CCR6 include LARC/MIP-3α/exodus. Ligands for CCR7 include ELC/MIP-3β. Ligands for CCR8 include I-309. Ligands for CXCR1 include IL-8 and GCP-2. Ligands for CXCR2 include IL-8, GRO-α/β/γ, NAP-2, ENA78 and GCP-2. Ligands for CXCR3 include IP10 and Mig. Ligands for CXCR4 include SDF-1. Ligands for CXCR5 include BCA-1/BLC. For example, SDF-1α, a CXC chemokine, is the natural ligand for CXCR4 (also called fusin, LESTR and HUMSTR). T-tropic HIV strains bind to CD4 and then depend on subsequent binding to the CXCR4 receptor for entry into cells. SDF-1 thus has the potential to block HIV binding to CXCR4. The chemokine family of proteins are thus prime targets for development of lead compounds in characterizing and treating such disorders.

The characteristic pattern of cysteine residues in chemokines is particularly well suited to the systematic production of focused sets of modular hybrid chemokine analogues by native chemical synthesis. Chemokines represent a class of proteins with varied overlapping reactivity and functions, both at the receptor and cell levels. Several chemokine structures have been solved by NMR and X-ray crystallography. The three-dimensional structures are highly homologous and represent an invariant peptide backbone or scaffolding. The structures also show a highly conserved set of amino acids forming the hydrophobic core. Because of the structural homology across approximately 65 chemokines (to date), the various segments of the chemokines are particularly well suited for swapping of functional modules (i.e., cross-over synthesis) between each other to construct novel chemokine libraries, and identify different activities related to structure and function.

Except for the CXC chemokine PBSF, consensus patterns of the CXC chemokines have been shown, as illustrated below beginning from the cysteines of the N-terminus:

$_n$X(1,8)-C-X-C-[LIVM]-X(5,6)-[LIVMFY]-X(2)-[RKSEQ]-X-[LIVM]-X(2)-[LIVM]-X(5)-[SAG]-X(2)-CX(3)-[EQ]-[LIVM]-X(2)-X(9,10)-CL-[DN](SEQ ID NO: 2)

Consensus patterns of the CC chemokines also have been shown, as illustrated below beginning from the cysteines of the N-terminus:

$_n$X(1,9)-C-C-[LIVMFYT]-X(5,6)-[LIVM]-X(4)-[LIVMF]-X(2)-Y-X(2,3)-[GSTN](2)-X(1,2)-C-X(3,4)-[SAG]-[LIVM]-X(2)- [FL]-X(5)- [RKTMF]-X(2)-C (SEQ ID NO: 2)

Since chemokines contain cysteine sites which are amenable to native chemical ligation, the modular chemokines can be readily synthesized in two or four segments without the need to introduce additional cysteines or use other ligation methods. As an example, cross-over chemokines produced using a two segment approach have an N-terminal segment from one chemokine and a C-terminal segment from another as shown in scheme (1) below. The novel proteins are assessed for different properties contributed from the original, parent chemokines.

and a cysteine. Typically, chemokines contain four cysteines and therefore can be made in five segments (four native ligations). As noted above, cysteines also may be designed into the structure to permit alternative ligation sites amenable to native ligation chemistry. Additionally, other types of ligation permit assembly of chemokines and other proteins at other sites.

The melanocortin family of receptor-ligands also are examples of proteins amenable to cross-over synthesis as exemplified above for the chemokines. For instance, the melanocortin receptors include the melanocyte melanocortin receptor (MC1R), MC2R (adrenocortical ACTH receptor), MCR3, MCR4 and MCR5 receptors. Ligands for various melanocortin receptors include agouti protein (AGP) and agouti-related proteins (AGRP). Of particular interest are analogues of AGRP, including minimized agouti-related proteins (MARP) as disclosed in Thompson et al., co-pending provisional patent application U.S. Ser. No. 60/079,957.

The cross-over proteins and libraries can be used in a variety of therapeutic applications. Preferred hybrid proteins are those comprising cross-over members of the chemokine family, and analogs derived therefrom. The modular chemokines of the invention may be used in a variety of therapeutic areas, including inflammation and infectious diseases such as AIDS, as well as in indications for hematopoiesis and chemoprotection. Modified derivatives of the native compounds also have been shown to effectively block the inflammatory effects of RANTES. Accordingly, they are useful for the treatment of asthma, allergic rhinitis, atopic dermatitis, atheroma/atheroschleosis, and rheumatoid arthritis. Chemokines also have been shown to inhibit HIV-1 infection in vitro. Additional cross-over proteins and librar-

```
                                    Scheme 1

Chemokine 1:
H₂N—AAAAAAAAAAAAAAAAAAAA-CBBBBBBBBBBBBBBBBBBBBB—COOH

Chemokine 2:
H₂N—RRRRRRRRRRRRRRRRRRRRR-CSSSSSSSSSSSSSSSSSSSSSSSS—COOH

Chemokine (1/2):
H₂N—AAAAAAAAAAAAAAAAAAAA-CSSSSSSSSSSSSSSSSSSSSSSSS—COOH

Chemokine (2/1):
H₂N—RRRRRRRRRRRRRRRRRRRRR-CBBBBBBBBBBBBBBBBBBBBB—COOH
```

Where the native chemokine sequences 1 and 2, where A, B, R, and S are arbitrary amino acids determined in the naturally occurring chemokine, and each can by synthesized by native chemical ligation of two segments, and C represents a Cysteine, the site which is amenable to native chemical ligation.

In accordance with Scheme 1, the N-terminal segment of chemokine 1 (fictitiously consisting of all A amino acids) can be ligated to the C-terminal segment of chemokine 1 (fictitiously consisting of cysteine (C) followed by all B amino acids). Likewise, chemokine 2 can be synthesized by the ligation of the N-terminal segment of chemokine 2 to the C-terminal segment of chemokine 2. Each chemokine folds into the natural, biologically-active protein. The cross-over chemokine (1/2) is made by ligating the N-terminal segment of chemokine 1 to the C-terminal segment of chemokine 2. Likewise, an additional unique crossover chemokine, chemokine (2/1) is made by ligating the N-terminus of chemokine 2 to the C-terminal segment in chemokine 1. The native chemical ligation can be applied between any residue ies of interest are cross-over members of agouti protein ligands for the melanocortin receptor family, including AGP and MARP that are useful for modulating satiety in a mammal or a disease state such as a wasting syndrome in a mammal including HIV wasting syndrome, cachexia, or quorexia. For instance, cross-over agouti proteins find use as leads in treating feeding disorders, obesity, and other disorders related to hypothalamic control of feeding. A wasting syndrome is an illness characterized by significant weight loss accompanied by other indicia of poor health, including poor appetite, gut disorder, or increased metabolic rate. Wasting syndromes include, but are not limited to, the wasting syndrome afflicting some patients diagnosed with Acquired Immune Deficiency Syndrome (AIDS) and various cancers. As methods of treating other symptoms of diseases such as AIDS progress, the incidence of wasting syndrome as the cause of death increases. Improved prophylaxis and treatment for HIV wasting syndrome is required (Kravick et al., *Arch. Intern. Med.* (1997) 157:2069–2073). Anorexia and cachexia are well-known results of cancer that contribute to morbidity and mortality (Simons et al, *Cancer* (1998) 82:553–560; Andrassy et al., *Nutrition* (1998) 14:124–129). The reasons for the significant weight loss are multiple and may be directly related to the tumor, such as increased metabolic rate, but also include decreased intake due to poor appetite or gut involvement. Further, excessive leptin-like signaling may contribute to the pathogenesis of wasting illness (Schwartz et al., *Pro. Nutr. Soc.* (1997) 56:785–791).

The invention further includes a pharmaceutical composition comprising a cross-over protein of the invention, such as one derived from a cross-over protein library of the invention. Also provided are kits having a cross-over protein of the invention, and/or or produced by a method(s) of the invention.

In applying the compounds of this invention to treatment of the above conditions, administration of the active compounds and salts described herein are preferably administered parenterally. Parenteral administration is generally characterized by injection, either subcutaneously, intramuscularly or intravenously, and can include intradermal or intraperitoneal injections as well as intrasternal injection or infusion techniques. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For parenteral administration there are especially suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilisate and can be made into a solution prior to parenteral administration by the addition of suitable solvents. Solutions such as are used, for example, for parenteral administration can also be used as infusion solutions. A more recently devised approach for parenteral administration employs the implantation of a slow-release or sustained-release system, such that a constant level of dosage is maintained. See, e.g., Higuchi et al., U.S. Pat. No. 3,710,795, which is hereby incorporated by reference.

The percentage of active compound contained in such parental compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.02–8% of the active agent in solution.

There are more than 65 known chemokines, and additional new sequences are being added to public genome databases at a rapid rate. Ligands for other therapeutically important receptors also are being identified and characterized at a significant rate. Construction of cross-over protein libraries can be used for the rapid conversion of genomic data into high-purity novel proteins that can be used contiguously, and also can be used for the preparation of a wide range of analogues by chemical modification, such as N-terminal modification. Modular protein libraries can be used to define protein structure-activity relationships and to identify new lead compounds for treatment of mammalian disorders. The construction of modular cross-over protein libraries also can be used to improve the therapeutic utility of a native protein by, for example, improving its binding affinity and specificity, or by increasing its circulating half life. The modular hybrid approach described here has widespread applications in analyzing important structural determinants in other classes of molecules. The novel molecules are useful for in vitro studies of viral infection and for therapies based on administration and over-expression of mutants or analogs of these chemokines. Modular synthesis of cross-over chemokines having a combination of cross-over activities obtained from CC or CXC chemokines can be used as novel therapeutic leads and to assess the structural basis of properties such as folding, stability, catalytic activity, binding. and biological action. The dual agonist activities of the modular chemokines are particularly suited as antagonist and/or agonist against HIV infection. Cross-over melanocortin receptor-specific ligands such as AGP protein, AGRP and MARP also are examples of therapeutic proteins accessible by the methods of the invention that can be used as novel therapeutic leads. Libraries of chemokines and agouti cross-over proteins generated by the chemical synthesis methods of the invention represent compound libraries having unprecedented focused diversity, high yield and purity, where the product is free of cellular contaminants.

Purity and yield are important for screening and therapeutic purposes. Very often quantity of a compound in a library is a limiting factor for the type and number of screening assays that can be employed. For example, the detection method typically is limited in part by the amount of a compound obtained from a library. In addition, purity is of critical important for efficacious screening of compounds in biological assays, to avoid skewed results contributed by impurities. Of course purity and yield is necessary when a cross-over protein is utilized for therapeutic purposes, so as to minimize contaminants and provide unlimited access to high quality and certified product. Since the libraries of the invention can be generated by chemical synthesis and ligation, yield and purity can be controlled.

The methods and compositions of the invention also can be exploited in screening and diagnostic assays, and are particularly amenable to resonance energy transfer assays employing FRET analyses. This includes access to donor-acceptor chromophore systems that can be used as a qualitative or a quantitative tool to detect and characterize interactions between a receptor-ligand system of interest. The principles and applications of employing resonance energy transfer systems are many and well known (Wu et al., supra). For instance, the cross-over protein ligands can be simultaneously constructed and labeled via native chemical ligation to create a chromophore donor/acceptor system that enables detection through FRET. Since measurement of energy transfer is based on fluorescence detection, the assays are highly sensitive and can be used to detect ligand binding. Since the time scale of resonance energy transfer is on the order of nanoseconds, many processes including slow conversion of conformers that are time-averaged in other techniques can be resolved. This approach can be used to infer the spatial relation between donor and acceptor chromophores to obtain structural information, including ligand-induced conformational changes. In addition to data acquisition with a conventional spectrophotofluorometer, the FRET methods can be adapted for multiple in vitro and in vivo assays including liquid chromatography, electrophoresis, microscopy, and flow cytometry etc. Thus, the present invention can be used for both in vitro and in vivo assays. The method also can be applied as a simple diagnostic tool, as well as used in the study of membrane structure and dynamics, or extend it to molecular interactions on cell surfaces or in single cells.

The following examples are presented to illustrate the invention and are not intended to be limiting.

EXAMPLES

Example 1

Identification of Functional Protein Modules for Synthesis of Cross-Over Chemokine Libraries Chemokine patterns are compared on a linear amino acid sequence level and on a three-dimensional structural level to identify functional protein modules for the modular synthesis of cross-over chemokine libraries. Functional protein modules corresponding to homologous regions among the native chemokines are identified by alignment of segments of RANTES, SDF-1α, and the virally encoded chemokines vMIP-I and vMIP-II (See FIG. 3). Macrophage Derived Chemokine (MDC) and the Kaposi's sarcoma-associated herpes virus (KSHV) vMIP-I and II chemokines also are compared. Sequence alignment of RANTES, SDF-1α and the viral chemokines against the RANTES three-dimensional structure (Brookhaven Protein Databank, Brookhaven National Labs, N.Y.) using LOOK® software (Molecular Applications Group, Palo Alto, Calif.) identified sections of sequences that correlated with functional sections relative to the folded chemokines. On a sequence level the chemokines are found to be divided into segments by the cysteines, typically at positions 8, 9, 34 and 50 relative to the functional molecules (positions 10, 11, 34 and 50, respectively, as depicted in FIG. 3). Each of the intervening segments is found to provide some part of overlapping binding sites for various receptors. The N-terminal segment (residues 1–8) has been shown to be important for receptor activation; truncation of the N-terminal segment can yield antagonists that bind but do not signal (e.g., RANTES, Arenzana-Selsdedos et al., Nature (1996) 383: 400). The second segment (residues 8–9) identified contains either 0, 1, or 3 amino acids. Although this segment is short, the CC-chemokines (zero amino acids in this segment) and the CXC-chemokines (one amino acid in this segment) bind to two different sets of receptors with no overlap between them. The third segment (residues 9–34) identified can be divided into two distinct regions. Segment (residues 9–22) interacts with the 7-transmembrane G-protein receptors. The segment (residues 23–34) is identified as comprising the dimer interface based upon comparison of the three-dimensional structures of CXC chemokines like IL8. The fourth segment (residues 35–50) is identified as comprising a central beta strand which contributes to the hydrophobic core and a region (43–49) which also interacts with the 7-transmembrane G-protein receptors. For IL-8 and GRO gamma, the regions 9–22 and 43–49 also have been shown to be important for determining binding to different receptors (Hammond et al., supra). The fifth segment (residues 51–75) is identified as containing a C-terminal helix which contributes to the hydrophobic core and contains a heparin-binding domain. Crossing-over the binding regions based upon location of the cysteines, permits the separation of the four regions most important for binding to the 7-transmembrane G-protein receptors: residues (1–8), (8–9), (9–23), and (43–49).

In addition, an asparagine to alanine substitution at position 33 of a synthetic SDF-1α has been shown to be a more potent activator of chemotaxis compared to the native SDF-1α sequence. This indicates that the N33A substitution improves receptor-mediated activation. The substituted amino acid precedes the central cysteine that approximately separates the chemokine into halves. Alignment of the CC chemokines in LOOK® with the seven-color scheme reveals that the N-terminus and the two amino acids before the central cysteine appeared to be relatively unique. The substitution at position 33 also may effect a putative switch for activating the receptor and/or agonist binding. Construction of modular chemokines comprising functional modules from RANTES and SDF-1α are used to characterize receptor activation and agonist/antagonist design.

Example 2

Modular Synthesis Of Cross-Over Chemokine Libraries

The cross-over chemokine libraries are chemically synthesized using solid phase and native chemical ligation at Xxx-Cys residues. SDF-1α has been synthesized by stepwise solid phase peptide chemistry (Bleul et al., Nature (1996) 382:829) and (Oberlin et al., Nature (1996) 382:833). SDF1-α also has been synthesized by native chemical ligation. These techniques are employed to construct MPBV/MPAV, RANTES/SDF-1α cross-over chemokines discussed in the examples that follow. See in-situ neutralization Boc-peptide synthesis as described in Schnolzer et al., Int. J Peptide Protein Res. (1992) 40:180; chemical synthesis and native ligation of proteins as described in Dawson et al., supra; Muir, (1993) Current Opinion Biochem. 4:420; Canne et al., J. Am. Chem. Soc (1995) 117:2998; Lu et al., J. Am. Chem. Soc. (1996) 118:8518; and Lu et al., Biochemistry (1997) 36(4):673; and thioester resins for Boc-peptide synthesis as described in Hono et al., Chem. Soc. Jpn. 64, 111 (1991); Tam et al., Proc. Natl. Acad. Sci USA (1995) 92:12485; and Canne et al., Tetrahedron Lett. (1995) 36:1217; and chemokines and assays as described in Baggiolini et al., Cytokine (1991) 3:165; Oppenheim, Adv. Exp. Med. Biol. (1993) 351:183; Sykes et al., Science (1994) 264:90; Clark-Lewis et al., J. Biol. Chem. (1994) 269:16075; and Hromas et al., Blood (1997) 89(9):3315.

Briefly, chemical synthesis is preformed using Boc protected amino acids obtained from AnaSpec (San Jose, Calif.), Bachem California (Torrance, Calif.), Bachem (Philadelphia, Pa.), NovaBiochem (San Diego, Calif.), Peninsula Laboratories (Belmont, Calif.) or Peptides International (Louisville, Ky.). Protected amino acids as follows: Arg(Tos), L-Asp(OChx), Asn(Xan), L-Glu(OChx), His (DNP), Lys(2ClZ), Ser(Bz), Thr(Bz), Tyr(2BrZ). DMF and DCM are HPLC grade and used as received. Trifluoroacetic acid is obtained from HaloCarbon (River Edge, N.J.).

Peptides are synthesized on a modified ABI430A instrument using in situ neutralization boc chemistry protocols. C-terminal segments are prepared on-OCH2Pam resins (ABI, Foster City, Calif.). N-terminal segments are prepared on α-thio-carboxylate-resin. Standard HF cleavage protocols are employed following N-terminal Boc removal and drying of the resin. HPLC purification is performed on Rainin HPLCs (Woburn, Mass.) using Vydac C4 (4.6 and 25 mm) or Dynamax C4 (4.6 mm or 2 in) columns with gradient elution (A: 0.1% TFA, B: ACN, 0.1% TFA). Electrospray mass spectrometry is performed on a Sciex API1 (PE-Sciex).

Ligation is performed at 4 mM peptide concentration in 6M guanidine. 0.1M phosphate, pH=7.0 in the presence of 33 mM thiophenol (Fluka, Switzerland) at room temperature. Ligation is monitored by HPLC and typically complete within 24 hours. Ligation is followed by HPLC purification and lyophilization as described above.

Folding of synthetic chemokines is conducted as follows. After purification, the full-length peptide is reduced at 1.0 mg/mL in 8M urea (Fluka, Switzerland), 0.1 M TRIS (Fluka, Switzerland), 5.37 mM EDTA (Fluka, Switzerland), pH=8.6 in the presence of 100 mM 2-mercaptoethanol (Fluka, Switzerland). Reduction occurs under a nitrogen atmosphere at 40° C. for one hour. After complete reduction, the mixture is diluted into the same buffer at 0.2 mg/mL with 18.7 mM oxidized glutathione (Sigma Chemical, St. Louis, Mo.). The solution is dispensed into a Spectrum Spectra/Por *7 dialysis membrane (Houston, Tex.) (MWCO=3500) and the bag placed in 1.0 L of initial dialysis buffer of 8M urea, 0.1M TRIS, 1 mM EDTA, 3 mM 2-mercaptoethanol, 1.3 mM oxidized glutathione, pH=8.6. Then, over a period of two days, 4 liters of 2M urea, 0.1M TRIS, pH=8.6 is pumped into the vessel containing the dialysis bag. Folding is monitored by HPLC and mass spectrometry and is usually complete after 3 buffer changes (3 liters).

Alternatively, full length peptide is reduced directly from the ligation conditions at 1 mg/mL in 6M guanidine.HCl (Fluka, Switzerland), 0.1M TRIS, pH=8.5 in the presence of 100 mM 2-mercaptoethanol. After purification on reversed phase HPLC and lyophilization, the peptide is oxidized at 1 mg/mL in 1M guanidine.HCl, 0.1M TRIS, pH=8.6 at room temperature in the presence of air. After stirring overnight, folding is complete. Alternatively, full length peptide preferably is folded in 2M guanidine.HCl, 0.1 M TRIS, pH 8 containing 8 mM cysteine and 1 mM cystine at 0.5 mg/ml at room temperature with stirring overnight.

Validation procedures used to confirm purity and chemical structure include HPLC, electrospray mass spectrometry, and peptide mapping. Biological activity of the cross-over chemokines is demonstrated following standard chemotaxis and receptor binding assays using recombinant or chemically synthesized MPBV, SDF-1α and/or RANTES as controls.

Example 3
Modular Synthesis of Cross-over Chemokines Comprising Functional Modules from vMIP-I And vMIP-II Novel viral cross-over chemokines are constructed by combining segments comprising functional modules from two related virally encoded chemokines. Functional protein modules corresponding to homologous binding sites on the surface of native chemokines are identified by alignment of segments (halves) of Macrophage Derived Chemokine (MDC) and the Kaposi's sarcoma-associated herpes virus (KSHV) chemokines against other known chemokines. Sequence alignment of the viral chemokines against the RANTES three-dimensional structure (Brookhaven Protein Databank, Brookhaven National Labs, NY) using LOOK® software identified sections of sequences that correlated with patches (putative binding sites) localized to the surface of the folded chemokines. Crossover chemokines are made by modular synthesis using native ligation at the central cysteine and folding of viral chemokine segments derived from vMIP-1 (MPAV) and vMIP-II (MPBV). The two unique crossover chemokines are designated MP(A/B)V and MP(B/A)V. The MP(A/B)V cross-over chemokine comprises the N-terminal segment from MPAV (amino acids 1–35) and the C-terminal segment of the MPBV (amino acids 38–74). The MP(B/A)V cross-over chemokine comprises the N-terminal segment from MPBV (amino acids 1–37) and the C-terminal segment of the MPAV (amino acids 36–71). The effect of these crossovers on the three-dimensional (tertiary) structure of a chemokine are evaluated relative to the three-dimensional scaffold, which represented separation of functional modules corresponding to the "N-terminal tail" and the "lower right side" in the N-terminal segment from the "front upper left" in the C-terminal segment. The amino acid sequences for four chemically synthesized chemokines are shown in Table II below and represent two of the native virally encoded chemokines MPAV and MPBV, and two of the cross-over chemokines corresponding to MP(A/B)V and MP (B/A)V.

TABLE II

Amino acid sequences of the native MPAV and MPBV molecules, and cross-over chemokines MP(A/B)V and MP(B/A)V.

MPAV (1–71) (SEQ ID NO:3):
AGSLVSYTPNSCCYGFQQHPPPVQILKEWYPTSPACPKPGVILL
TKRGRQICADPSKNWVRQLMQRLPAIA

MPBV (1–74) (SEQ ID NO:4):
GDTLGASWHRPDKCCLGYQKRPLPQVLLSSWYPTSQLCSKPG
VIFLTKRGRQVCADKSKDWVKKLMQQLPVTAR

MP (A/B) V(1–72) (SEQ ID NO:5):
AGSLVSYTPNSCCYGFQQHPPPVQILKEWYPTSPACSKPGVIFL
TKRGRQVCADKSKDWVKKLMQQLPVTAR

MP (B/A) V(1–73) (SEQ ID NO:6):
GDTLGASWHRPDKCCLGYQKRPLPQVLLSSWYPTSQLCPKPG
VILLTKRGRQICADPSKNWVRQLMQRLPAIA

Example 4
Modular Synthesis of Cross-Over Chemokines Comprising Functional Modules from SDF-1α and Rantes All CC and CXC chemokines contain four cysteines giving sites amenable to native chemical ligation at Xxx-Cys positions. Peptides corresponding to the N-terminal and C-terminal halves flanking the Cys positions are synthesized, purified and ligated following the scheme depicted in Tables III-V and FIGS. 1 and 2. In particular, SDF-1α (a CXC chemokine that binds to the CXCR4 receptor) and RANTES (a CC chemokine that binds to the CCR5 receptor) are employed in the modular synthesis of cross-over chemokines using eight N-terminal modules in various combinations with four C-terminal modules derived from these chemokines (see Tables IV and V). Additional diversity is incorporated into the N-terminal segment by the deletion of the "X" residue from the "CXC" module of SDF-1α and insertion of a residue between the "CC" module of RANTES, for a total of eight N-terminal modules. For example, in SDF-1α the N-terminal module corresponds to "KPVSLSYRCP" from which the P residue is deleted to give KPVSLSYRC (i.e., deletion of the "X" residue from the "CXC" module); in RANTES the N-terminal module corresponds to "SPYSSDTTPC" into which a P residue is inserted to yield "SPYSSDTTPCP" (i.e., insertion of an "X" residue between the "CC" module) (See Table IV). Native chemical ligation technology is used to synthesize the two modified native and 30 hybrid chemokines between SDF-1α and RANTES. In addition, solid phase chemical ligation is used to construct the two modified native molecules for comparison to molecules prepared by native chemical ligation. The cross-over chemokines synthesized are assayed for binding to the CXCR4 and CCR5 receptors, and the residues directly involved in binding to the two different receptors are identified (see Example 5). This library of molecules also is used to probe the structure and function of the N-terminal CXC or CC modules, the hydrophobic pocket, and the C-terminal regions between the two classes of chemokines. In addition, the hybrid chemokines are screened to identify those molecules which display "dual functionality," i.e., the ability to bind both CXCR4 and CCR5. Selection of the hybrid chemokines is characterized using IH-NMR and other biophysical techniques. This first group of molecules are used in a second round of iteration (for example N-terminal modifications) to further improve binding to the receptors. Use of the cross-over chemokine molecules also are assayed for blocking of CXCR4 and CCR5 for prevention of HIV entry into cells, as binding of chemokines to CXCR4 and CCR5 has been shown to block HIV entry into cells (Simons et al., Science (1997) 275:1261–1264) (see Example 5). Other biological assays may be used to determine general structure-function relationships within chemokine molecules.

TABLE III

| Amino acid sequences for native and base synthetic SDF-1 and RANTES |
|---|
| SDF-1α (human residues 1–93): MNAKVVVVLVLVLTALCLSDGKPVSLSYRCPCRFFESHVAPA NVKHLKILNTPNCALQIVARLKNNNRQVCIDPKLKWIQEYLEK ALNKRFKM (SEQ ID NO:7) |

TABLE III-continued

| Amino acid sequences for native and base synthetic SDF-1 and RANTES |
|---|
| SDF-1α (1–67) (synthetic base molecule missing pre-sequence/N-terminal residues 1–21 and C-terminal residues 89–93): KPVSLSYRCPCRFFESHVARANVKHLKILNTPNCALQIVARLKN NNRQVCIDPKILKWIQEYLEKALN (SEQ ID NO:8) |
| RANTES (human residues 1–91): MKVSAARLAVILIATALCAPASASPYSSDTTPCCFAYIARPLPRA HIKEYFYTSGKCSNPAVVFVTRKNRQVCANPEKKWVREYINSL EMS (SEQ ID NO:9) |
| RANTES (1–68) (synthetic base molecule missing pre-sequence/N-terminal residues 1–23): SPYSSDTTPCCFAYIARPLPRAHIKEYFYTSGKCSNPAVVFVTRK NRQVCANPEKKWVREYINSLEMS (SEQ ID NO:10) |

TABLE IV

Modular synthesis of cross-over chemokines using eight N-terminal modules in combination with four C-terminal modules to construct cross-over chemokine molecules.

| Ref | Amino Acid Sequence | SEQ ID NO |
|---|---|---|
| 8X N-terminal modules: | | |
| SS | KPVSLSYRCPCRFFESHVARANVKHLKILNTPN | (SEQ ID NO: 11) |
| S'S | KPVSLSYRCCRFFESHVARANVKHLKILNTPN | (SEQ ID NO: 12) |
| SR | KPVSLSYRCPCFAYIARPLPRAHIKEYFYTSGK | (SEQ ID NO: 13) |
| S'R | KPVSLSYRCCFAYIARPLPRAHIKEYFYTSGK | (SEQ ID NO: 14) |
| RR | SPYSSDTTPCCFAYIARPLPRAHIKEYFYTSGK | (SEQ ID NO: 15) |
| R'R | SPYSSDTTPCPCFAYIARPLPRAHIKEYFYTSGK | (SEQ ID NO: 16) |
| RS | SPYSSDTTPCCRFFESHVARANVKHLKILNTPN | (SEQ ID NO: 17) |
| R'S | SPYSSDTTPCPCRFFESHVARANVKHLKILNTPN | (SEQ ID NO: 18) |
| 4X C-terminal modules: | | |
| SS | CALQIVARLKNNNRQVCIDPKLKWIQEYLEKALN | (SEQ ID NO: 19) |
| SR | CALQIVARLKNNNRQVCANPEKKWVREYINSLEMS | (SEQ ID NO: 20) |
| RS | CSNPAVVFVTRXNRQVCIDPKLKWIQEYLEKALN | (SEQ ID NO: 21) |
| RR | CSNPAVVFVTRKNRQVCANPEKKWVREYINSLEMS | (SEQ ID NO: 22) |

TABLE V

Amino acid sequences for SDF-1α/RANTES cross-over molecules
Combination of 8X N-terminal and 4X C-terminal modules:

| | | | |
|---|---|---|---|
| SSSS (control) | SRSS | RRSS | RSSS |
| SSSR | SRSR | RRSR | RSSR |
| SSRS | SRRS | RRRS | RSRS |
| SSRR | SRRR | RRRR (control) | RSRR |
| S'SSS (-Pro control) | S'RSS | R'RSS | R'SSS |
| S'SSR | S'RSR | R'RSR | R'SSR |

TABLE V-continued

Amino acid sequences for SDF-1α/RANTES cross-over molecules
Combination of 8X N-terminal and 4X C-terminal modules:

| | | | |
|---|---|---|---|
| S'SRS | S'RRS | R'RRS | R'SRS |
| S'SRR | S'RRR | R'RRR | R'SRR |
| | | (+Pro control) | |

SSSS:
KPVSLSYRCPCRFFESHVARANVKHLKILNTPNCALQLVARLKN (SEQ ID NO: 23)
NNRQVCIDPKLKWIQEYLEKALN

SSSR:
KPVSLSYRCPCRFFESHVARANVKHLKILNTPNCALQIVARLKN (SEQ ID NO: 24)
NNRQVCANPEKKWVREYINSLEMS

SSRS:
KPVSLSYRCPCRFFESHVARANVKHLKILNTPNCSNPAVVFVTR (SEQ ID NO: 25)
KNRQVCIDPKLKWIQEYLEKALN

SSRR:
KPVSLSYRCPCRFFESHVARANVKHLKILNTPNCSNPAVVFVTR (SEQ ID NO: 26)
KNRQVCANPEKKWVREYINSLEMS

S'SSS:
KPVSLSYRCCRFFESHVARANVKHLKILNTPNCALQIVARLKN (SEQ ID NO: 27)
NNRQVCIDPKLKWIQEYLEKALN

SSSR:
KPVSLSYRCCRFPESHVARANVKHLKILNTPNCALQIVARLKN (SEQ ID NO: 28)
NNRQVCANPEKKWVREYINSLEMS

SSRS:
KPVSLSYRCCRFFESHVARANVKHLKILNTPCNSNPAVVFVTR (SEQ ID NO: 29)
KNRQVCIDPKLKWIQEYLEKALN

S'SRR:
KPVSLSYRCCRFFESHVARANVKHLKILNTPNCSNPAVVFVTR (SEQ ID NO: 30)
KNRQVCANPEKKWVREYINSLEMS

SRSS:
KPVSLSYRCPCFAYIARPLPRAHIKEYFYTSGKCALQIVARLKN (SEQ ID NO: 31)
NNRQVCIDPKLKWIQEYLEKALN

SRSR:
KPVSLSYRCPCFAYIARPLPRAHLKEYFYTSGKCALQIVARLKN (SEQ ID NO: 32)
NNRQVCANPEKKWVREYINSLEMS

SRRS:
KPVSLSYRCPCFAYIARPLPRAHIKEYFYTSGKCSNPAVVFVTR (SEQ ID NO: 33)
KNRQVCIDPKLKWIQEYLEKALN

SRRR:
KPVSLSYRCPCFAYIARPLPRAHIKEYFYTSGKCSNPAVVFVTR (SEQ ID NO: 34)
KNRQVCANPEKKWVREYINSLEMS

S'RSS:
KPVSLSYRCCFAYIARPLPRAHIKEYFYTSGKCALQIVARLKNN (SEQ ID NO: 35)
NRQVCIDPKLKWIQEYLEKALN

S'RSR:
KPVSLSYRCCFAYIARPLPRAHIKEYFYTSGKCALQIVARLKNN (SEQ ID NO: 36)
NRQVCANPEKIKWVREYINSLEMS

S'RRS:
KPVSLSYRCCFAYIARPLPRAFIIKEYFYTSGKCSNPAVVFVTRK (SEQ ID NO: 37)
NRQVCIDPKLKWIQEYLEKALN

S'RRR:
KPVSLSYRCCFAYIARPLPRAHIKEYFYTSGKCSNPAVVFVTRK (SEQ ID NO: 38)
NRQVCANPEKKWVREYTNSLEMS

TABLE V-continued

Amino acid sequences for SDF-1α/RANTES
cross-over molecules
Combination of 8X N-terminal and 4X
C-terminal modules:

RRSS:
SPYSSDTTPCCFAYIARPLPRAHIKEYFYTSGKCALQIVARLKNN(SEQ ID NO: 39)
NRQVCIDPKLKWIQEYLEKALN

RRSR:
SPYSSDTTPCCFAYIARPLPRAHIKEYFYTSGKCALQIVARLKNN(SEQ ID NO: 40)
NRQVCANPEKKWVREYTNSLEMS

RRRS:
SPYSSDTTPCCFAYIARPLPRAHIKEYFYTSGKCSNPAVVFVTRK(SEQ ID NO: 41)
NRQVCIDPKLKWIQEYLEKALN

RRRR:
SPYSSDTTPCCFAYIARPLPRAHIKEYFYTSGKCSNPAVVFVTRK(SEQ ID NO: 42)
NRQVCANPEKXWVREYINSLEMS

R'RSS:
SPYSSDTTPCPCFAYIARPLPRAHIKEYFYTSGKCALQIVARLKN(SEQ ID NO: 43)
NNRQVCIDPKLKWIQEYLEKALN

R'RSR:
SPYSSDTTPCPCFAYIARPLPRAHIKEYFYTSGKCALQIVARLKN(SEQ ID NO: 44)
NNRQVCANPEKKWVREYINSLEMS

R'RRS:
SPYSSDTTPCPCFAYIARPLPRAHIKEYFYTSGKCSNPAVVFVTR(SEQ ID NO: 45)
KINRQVCIDPKLKWIQEYLEKALN

R'RRR:
SPYSSDTTPCPCFAYIARPLPRAHIKEYFYTSGKCSNPAVVFVTR(SEQ ID NO: 46)
KNRQVCANPEKKWVREYINSLEMS

RSSS:
SPYSSDTTPCCRFFESHVARANVKHLKILNTPNCALQIVARLICN(SEQ ID NO: 47)
NNRQVCLDPKLKWIQEYLEKALN

RSSR:
SPYSSDTTPCCRFFESHVARANVKHLKILNTPNCALQIVARLKN (SEQ ID NO: 48)
NNRQVCANPEKKWVREYINSLEMS

RSRS:
SPYSSDTTPCCRFFESHVARANVKHLKILNTPNCSNPAVVFVTR (SEQ ID NO: 49)
KNRQVCIDPKLKWIQEYLEKALN

RSRR:
SPYSSDTTPCCREFESHVARANVKHLKILNTPNCSNPAVVFVTR (SEQ ID NO: 50)
KNRQVCANPEKKWVRLEYINSLEMS

R'SSS:
SPYSSDTTPCPCRFFESHVARANVKHLKILNTPNCALQIVARLK (SEQ ID NO: 51)
NNNRQVCIDPKLKWIQEYLEKALN

R'SSR:
SPYSSDTTPCPCRFFESHVARANVKHLKILNTPNCALQIVARLK (SEQ ID NO: 52)
NNNRQVCANPEKKWVREYINSLEMS

R'SRS:
SPYSSDTTPCPCRFFESHVARANVKHLKILNTPNCSNPAVVFVT (SEQ ID NO: 53)
RKNRQVCIDPKLKWIQEYLEKALN

R'SRR:
SPYSSDTTPCPCRFFESHVARANVKHLKILNTPNCSNPAVVFVT (SEQ ID NO: 54)
RKNRQVCANPEKKWVREYINSLEMS

Figure 4:
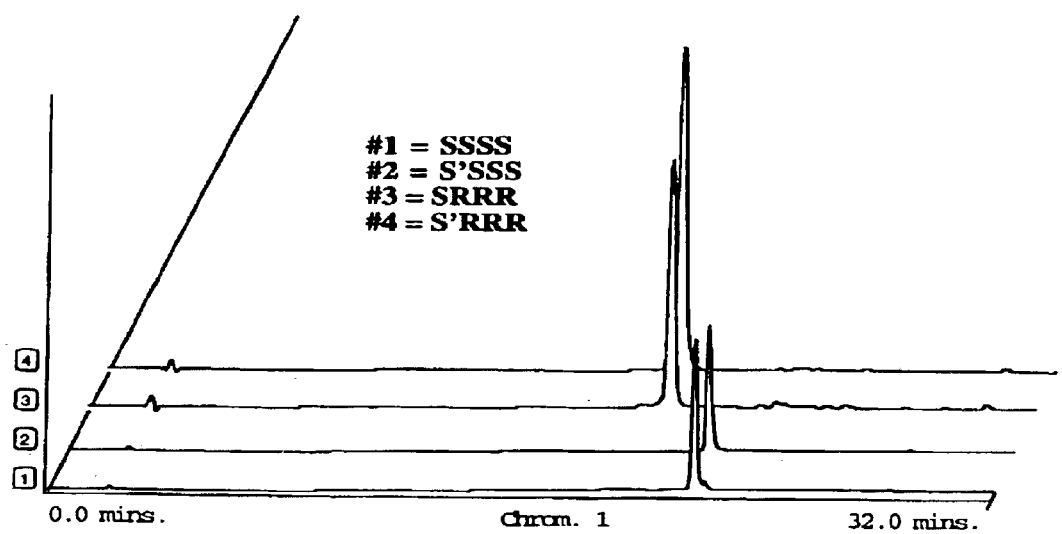
FIG. 4 shows analytical HPLC chromatograms for SSSS (control) and S'SSS, SRRR, and S'RRR modular chemokines; conditions: C4 reversed-phase HPLC column running a gradient of 5%–65% acetonitrile versus water containing 0.1% TFA, over 30 minutes, with detection at 214 nm.
Figure 5:
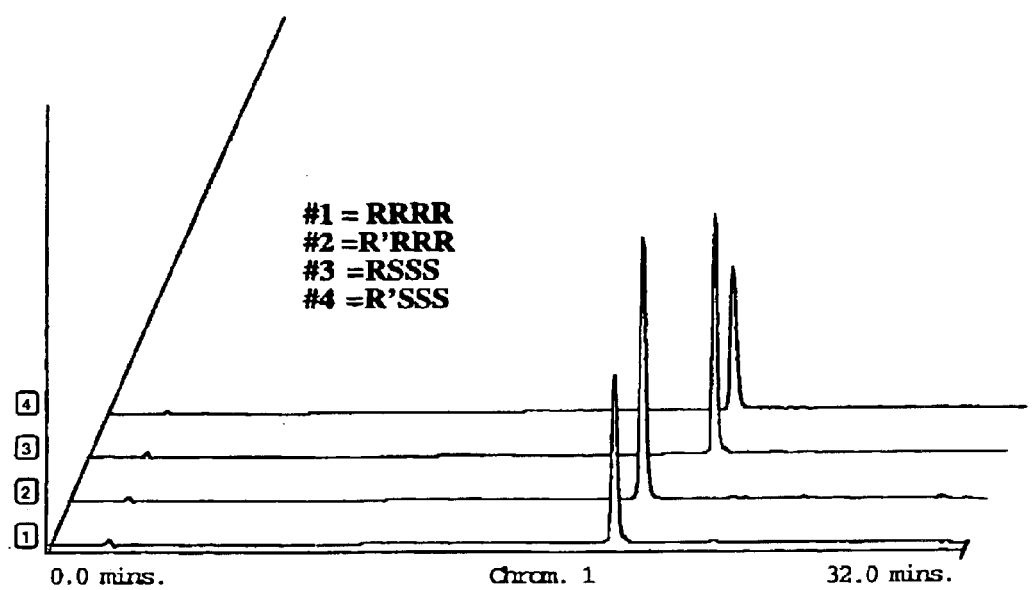
FIG. 5 shows analytical HPLC chromatograms for RRRR (control) and R'RRR, RSSS, and R'SSS modular chemokines; conditions: C4 reversed-phase HPLC column running a gradient of 5%–65% acetonitrile versus water containing 0.1% TFA, over 30 minutes, with detection at 214 mm.

Ligation and proper folding of a small library of cross-over chemokines are demonstrated in FIGS. 4–5, which show analytical HPLC for the SSSS (control), S'SSS (-Pro control), SRRR, S'RRR, RRRR (control), R'RRR (-Pro control), RSSS, and R'SSS chemokines depicted in Table V. Analytical HPLC also demonstrates variable separation properties among the cross-over chemokines, reflecting a likely difference in in vivo functionality. The calculated molecular weight (MW) of the expected cross-over protein ligation products and the actual MW determined by electrospray mass spectroscopy show a high level of agreement (See, e.g., Table VI).

TABLE VI

Calculated and Measured Molecular
Weights for Modular Cross-Over Chemokines

| Modular<br>Chemokine | Calculated<br>MW (Dalton) | Measured<br>MW (Dalton) |
|---|---|---|
| SSSS (control) | 7788.28 | 7789.29 |
| S'SSS (−Pro control) | 7691.16 | 7692.63 |
| SRRR | 7939.34 | 7939.96 |
| S'RRR | 7842.22 | 7842.09 |
| RRRR (control) | 7847.06 | 7848.36 |
| R'RRR (+Pro control) | 7944.17 | 7945.63 |
| RSSS | 7696.00 | 7695.06 |
| R'SSS | 7793.12 | 7791.96 |

Example 5
Cross-Over Chemokine Assays
Chemotaxis Assays:

Human peripheral blood leukocytes are isolated from normal donors according to established protocols for purification of monocytes, T lymphocytes and neutrophils. A panel of CC and CXC chemokine receptor-expressing test cells is constructed and evaluated following exposure to serial dilutions of individual compounds from the library of cross-over chemokines RANTES/SDF-1α, MP(A/B)V and MP(B/A)V. Synthetic native RANTES, SDF-1α, MPAV and MPBV are used as controls. The panel of cells represent human kidney embryonic epithelial (HEK) 293 cells transfected with expression cassettes encoding various chemokine receptors including CXCR4/Fusion/LESTR, CCR3, CCR5, CXC4 (these cells are available from various commercial and/or academic sources or can be prepared following standard protocols). Leukocyte migration relative to the transfected HEK cells is evaluated using a 48-well microchamber; migration of the receptor transfected HEK 293 cells also is assessed by the 48-well microchamber technique with the polycarbonate filters (10 um pore-size) precoated with Collagen type I (Collaborative Biomedical Products, Bedford, Mass.)(Neote et al., *Cell* (1993) 72:415–425; Risau et al., *Nature* (1997) 387:671–674; Angiololo et al., *Annals NY Acad Sci.* (1996) 795:158–167; Friedlander et al., *Science* (1995) 870:1500–1502). The results are expressed as the chemotaxis index (CI) representing the fold increase in the cell migration induced by stimuli versus control medium. All experiments are performed at least two times and results from one experiment are shown. The statistical significance of the difference between migration in response to stimuli and control are accessed by Student's T test.

Receptor Binding Assays:

Receptor binding assays are performed using a single concentration of $^{125}$I labeled chemokines in the presence of increasing concentrations of unlabeled ligands following standard protocols. The binding data are analyzed, for example, with a computer program such as LIGAND (P. Munson, Division of Computer Research and Technology, NIH, Bethesda, Md.). The binding data are subjected to Scatchard plots analysis with both "one site" and "two site" models compared to native leukocytes or the panel of receptor-transfected HEK cells expressing CXCR4, CCR3, CCR5 or CXC4. The rate of competition for binding by unlabeled ligands is calculated with the following formula: % inhibition=1-(Binding in the presence of unlabeled chemokine/binding in the presence of medium alone)×100.

HIV-1 Inhibition Assays:

Chemokine receptors act as co-receptors for human immune deficiency virus type (HIV)-1 entry into CD4+cells. The CC chemokines MIP-1A, MIP-1B, RANTES and eotaxin can suppress infection by some strains of HIV in PBMCs and chemokine receptor transfected cell lines. The viral-produced chemokine vMIP-1 inhibits some primary non-syncytium inducing (NSI) HIV strains when co-transfected with the NSI strain HIV-1 co-receptor CCR5. CCR3 is the predominant chemokine receptor through which eotaxin, RANTES and other CC chemokines activate eosinophils. RANTES and MIP-1A also can utilize the CCR1 receptor that is expressed on eosinophils. In addition, synthetic N-terminal variants of CC (e.g. Met-RANTES) and CXC (e.g. IL-8) chemokines function as receptor antagonists on eosinophils and neutrophils, whereas the native structures do not. Similarly, the CXC chemokine SDF-1α is a potent chemoattractant for leukocytes through activation of the receptor CXCR4/Fusin/LESTR, which is a fusion co-factor for the entry of HIV-1. CXCR4 mediated HIV-1 fusion can be inhibited in some cells by SDF-1α. Thus, despite the sequence similarities between certain chemokines of the same family, the binding and antagonist/agonist properties for HIV infection vary significantly.

Compounds from the library of cross-over chemokines RANTES/SDF-1α, MP(A/B)V and MP (B/A)V are screened for receptor usage, inhibition of HIV infection, potency and breadth of activity against HIV infection, induction of calcium mobilization and angiogenesis. The assays are used to evaluate suppression of HIV-I infection/replication in U87/CD4 cells (a human glioma cell line) expressing HIV-1 co-receptors and also in primary peripheral blood mononuclear cells (PBMCs).

The receptor-transfected U87/CD4 cells are obtainable by transfecting cells with an expression cassette encoding the respective receptors following standard protocols. The cells are maintained in Dulbecco's Minimal Essential Medium containing 10% FCS, glutamine, antibiotics, 1 ug/ml puromycin (Sigma Chemicals) and 300 ug/ml neomycin (G418; Sigma) and split twice a week. PBMCs are isolated from healthy blood donors by Ficoll-Hypaque centrifugation, then stimulated for 2–3 days with phytohemagglutinin (PHA) (5ug/ml) and IL-2 (100 U/ml)(Simmons, et al, *J. Viorol* (1996) 70:8355–8360). CD4+ T-cells are purified from the activated PBMC by positive selection using anti-CD4 immunomagnetic beads (DYNAL Inc.), screened for CCR-5 defective alleles, and cells from allele defective or wild-type donors used depending on the assay. HIV isolates are obtainable from various sources including the NIAID HIV-1 Antigenic Variation study, or from similar programs organized by the US Department of Defense or the World Health Organization. Phenotypes of test viruses are tested by their ability to form syncytia (SI) in MT-2 cells that are cultured in RPMI 1640 medium containing 10% fetal calf serum (FCS), glutamine and antibiotics. and split twice a week. Recombinant human CC-chemokines MIP-1A, MIP-1B and RANTES are obtainable from R&D Systems Inc. (Minneapolis). Synthetic SDF-1α stocks are obtainable from Gryphon Sciences (M.A.S. and D.A.T.) and Berlex Biosciences (R.H.). Chemokine stocks are compared for purity and potency.

Assay for Inhibition of HIV Infection:

Compounds from the library of cross-over chemokines RANTES/SDF-1α, MP(A/B)V and MP (B/A)V are tested against a panel of U87/CD4 cells stably expressing either CCR3, CCR5, CXC4 or CXCR4 receptors exposed to HIV-1/NSI strains SL-2 and SF162 (macrophage- tropic strains that utilize the RANTES, MIP-1α and MIP-1β receptor CCR5 to gain entry into CD4+cells) and the dual-tropic syncytium inducing (SI) strains 89.6 and 2028 (SI dual tropic strains that can use CXCR4 and CCR3 in addition to CCR5 for entry). Lymphocytes and CD4+ T-cells from donors also are tested. Serial concentrations ranging from 0 to 500 nM of the cross-over proteins are used. RANTES, MPBA, MPBV and SDF-1α are used as controls. Inhibition of HIV infection is reported as a percentage of infection relative to modular protein and control concentrations.

Purified lymphocytes are stimulated with PHA (0.5ug/ml) and cultured for 2–3 days at $2\times10^6$/ml in medium containing IL-2 (Boeringer-Mannheim, 20 U/ml) before being used in infection assays. Cells are pre-treated with appropriate concentrations of chemokines for 30 minutes at 37° C. Approximately 400–1000 TCID of virus are added to an appropriate volume and incubated at 37° C. for 3 hours. Cells are then washed 4 times and resuspended in an appropriate volume of media containing IL-2 and relevant chemokine at the appropriate concentration. Cells are fed every 3 days with fresh medium contain IL-2 and chemokine. From days 3 through 7 post-infection, the cultures are examined microscopically for syncytium formation and the supernatant analyzed for p24 antigen production using an enzyme linked immunoabsorbent assay (ELISA)(McKnight et al., *Virology* (1994) 201:8–18). Inhibitory doses a calculated relative to the final concentration of chemokine in the culture on day 0. Virus production in the absence of chemokine is designated as 100%, and the ratios of p24 antigen production in chemokine-containing cultures calculated relative to this percentage. The chemokine concentrations (pg/ml) causing 50% and 90% reduction in p24 antigen production are determined by linear regression analysis. If the appropriate degree of inhibition is not achieved at the highest or lowest chemokine concentration, a value of>or<is recorded.

Virus infectivity on the receptor expressing U87/CD4 cells is assessed by focus-forming units (FFU) (Simmons, et al., *Science* (1997) 276:276–279). The FFU for viruses using more than one co-receptor is assessed separately for each appropriate co-receptor expressing U87/CD4 cell type. Cells are seeded into 48 well trays at $1\times10^4$ cells/well overnight. The cells are then pre-treated for 30 minutes at 37° C. with appropriate concentrations of chemokine in 75ul. 100 FFU of each virus in 75ul is added and incubated for 3 hours at 37° C. Cells are washed 3 times and 500ul of medium containing the appropriate chemokine at the correct concentration is added. After 5 days the cells are fixed for 10 minutes in cold acetone:methanol (1:1) and analyzed for p24 antigen production. Standard errors are estimated from duplicate wells and results presented are representative of three separate experiments.

Assay for Breadth and Potency of Cross-Over Chemokines Against HIV Infection:

The breadth and potency of the inhibitory actions of compounds from the library of cross-over chemokines RANTES/SDF-1α, MP(A/B)V and MP (B/A)V are tested against native CC-chemokines (MIP-1A, MIP-1B and RANTES) for M-tropic primary isolates of HIV-1, and against a native CXC-chemokine (SDF-1α) for T-tropic isolates in mitogen-stimulated primary CD4+ T-cells. The cross-over chemokines are evaluated for their potency and spectrum of agonistic activity against HIV-1 strains relative to the native CC- and CXC-chemokines to identify the most active inhibitor of HIV-1 replication and the best template for therapeutic development. The properties and activities of M-Tropic and T-tropic primary HIV-1 isolates are recorded and compared to inhibition of infection by exposure to the cross-over chemokines relative to the HIV isolate designation, genetic subtype, and phenotype determined by ability of an isolate to form (SI) or not form (NSI) syncytia in MT-2 cells, the ability of an isolate to replicate efficiently in activated CD4+ T-cells from individuals homozygous for either wild-type or γ-32 CCR5 alleles, and the ability of an isolate to replicate in U87/CD4 cells stably expressing either CCR5 or CXCR4. The median ID50 and ID90 values (ng/ml) are calculated for each sample. A value of>indicates that 50% or 90% inhibition is not achieved at a chemokine concentration of the highest tested in any experiment. A value of<indicates that 50% or 90% inhibition is always achieved at a chemokine concentration of the lowest tested. The genetic subtypes of the test isolates and their abilities to use CXCR4 and CCR5 to enter transfected U87MG-CD4 cells are also compared. The means from two independent experiments are compared. FACS analysis of CCR5 and CXCR4 receptor expression levels, and/or competitive inhibition assay of cross-over chemokines and receptor down-regulation also may be tested following standard protocols (Wu et al., *J. Exp. Med.* (1997) 185:168–169; and Trkola et al., *Nature* (1996) 384:184–186).

Assay for Measuring Changes in Intracellular Calcium Concentration ([Ca2+]):

Calcium mobilization is indicative of receptor binding. Compounds from the library of cross-over chemokines RANTES/SDF-1α, MP(A/B)V and MP (B/A)V are assayed for calcium mobilization in purified neutrophils and eosinophils following standard protocols (Jose et al., *J Exp Med* (1994) 179:881–887). Purified neutrophils or eosinophils are incubated with fura-2 acetoxymethyl ester (1–2.5uM), washed 3 times in 10 mM PBS (without Ca2+/Mg2+)+0.1% BSA (200 ×g, 8 min), and finally resuspended at $2\times10^6$ cells/ml in 10 mM PBS (without Ca2+/Mg2+)+0.25% BSA+10 mM HEPES+10 mM glucose. Aliquots of cells are placed in quartz cuvettes and the external Ca2+ concentration adjusted to 1 mM with $CaCl_2$ Changes in fluorescence are measured at 37° C. using a fluorescence spectrophotometer at excitation wavelengths 340 nm and 380 nm and emission wavelength 510 nm. [Ca2+] levels are calculated using the ratio of the two fluorescence readings and a K for Ca2+ at 37° C. of 224 nM.

CAM Assay for Angiogenic Activity:

Angiogenic activities of compounds from the library of cross-over chemokines RANTES/SDF-1α, MP(A/B)V and MP (B/A)V are evaluated by the chick chorioallantoic membrane (CAM) assay (Oikawa et al., *Cancer Lett* (1991) 59:57–66). Native chemokines are used as controls. Fertilized Plymouth Rock x while Leghorn eggs are incubated at 37° C. in a humidified atmosphere (relative humidity, approx. 70%). Test samples are dissolved in sterile distilled water or PBS. Sterilized sample solution is mixed with an equal volume of autoclaved 2% methylcellulose. Additional controls are prepared with vehicle only (1% methylcellulose solution). 20ul of the sample solution is dropped on parafilm and dried up. The methylcellulose disks are stripped off from the parafilm and placed on a CAM of a 10 or 11 day old chick embryo. After 3 days, the CAMs are observed by means of an Olympus stereoscope. A 20% fat emulsion (Intralipos 20%, Midori-Juji, Osaka, Japan) is injected into the CAM to increase the contrast between blood and surrounding tissues (Danesi et al., *Clin Cancer Research* (1997) 3:265–272). The CAMs are photographed for evaluation of angiogenic response. Angiogenic responses are graded as negative, positive or unclear on the basis of infiltration of blood vessels into the area of the implanted methylcellulose disk by different observers.

As exemplified above, modular protein libraries comprising cross-over molecules are constructed. The cross-over libraries find use in identifying novel proteins having crossover activities contributed by a combination of individual functional protein modules from two or more distinct proteins of the same family or class. The methods of the invention can be readily adapted and integrated with genomic sequencing and bioinformatics to prepare novel combinatorial modular protein libraries for identifying new drug candidates, and for evaluating and validating the physiological relevance of the new targets. This approach represents an advance over traditional discovery protocols that rely on native, historical, and/or random synthetic libraries subjected to mass screening. Generation of modular protein libraries representing a focused set of molecules decreases the time and cost of discovering novel therapeutic agents for multiple disease states. The modular synthesis approach and the construction of cross-over protein libraries greatly expands the range of compounds available for biological screening and discovery of pharmaceutical agents.

REFERENCES

1. Andrassy et al., *Nutrition* (1998) 14:124–129
2. Angiololo et al., *Annals NY Acad. Sci.* (1996) 795:158–167
3. Arenzana-Selsdedos et al., *Nature* (1996) 383:400
4. Ausubel et al., (1989) "Current Protocols in Molecular Biology," Green Publishing Associates and Wiley Interscience, New York
5. Baggiolini et al, *Cytokine* (1991) 3:165
6. Ben-Efraim et al., *Biochemistry* (1994) 33:6966
7. Benson et al., *Nucleic Acids Res.* (1998) 28(1):1–7
8. Berlman et al., *Energy Transfer Parameters of Aromatic Compounds*, (1973) Academic Press, New York
9. Bleul et al., *Nature* (1996) 382:829
10. Brenner et al., *Proc. Natl. Acad. Sci. U.S.A.* (1992) 89:5381–5383
11. Bunin et al., *J. Am. Chem. Soc.* (1992) 114:10997–10998
12. Bunin et al., *Proc. Natl. Acad. Sci. USA* (1993) 91:4708–4712
13. Canne et al., *J Am. Chem. Soc* (1995) 117:2998
14. Canne et al., American Peptide Symposium, Nashville, June 1997
15. Canne et al., *Tetrahedron Lett.* (1995) 36:1217–1220
16. Clark-Lewis et al., *J Biol. Chem.* (1994) 269:16075
17. Cwirla et al., *Proc. Natl. Acad. Sci. USA* (1990) 87:6378–6382
18. Danesi et al., *Clin. Cancer Res.* (1997) 3:265–273
19. Dawson et al., *Science* (1994) 266:776–779
20. Devlin et al., *Science* (1990) 249:404–406
21. DeWitt et al., *Proc. Natl. Acad. Sci. U.S.A.* (1993) 90:6909–6913
22. dos Remedios et al., *J Muscle Res Cell Motility* (1987) 8:97–117
23. Englebretson et al., *Tet. Letts.* (1995) 36(48):8871–8874
24. Fairclough et al., *Meth Enzymol* (1978) 48:347–379
25. Friedlander et al., *Science* (1995) 870:1500–1502
26. Furka et al., Abstr. 14th Int. Congr. Biochem., Prague, Czechoslovakia, Vol 5, pg 47. Abstr. 10th Intl. Symp. Med. Chem., Budapest, Hungary, (1988), pg 288
27. Gallop et al., *J Med. Chem.* (1994) 37:1233–1251
28. Gaertner et al., *Bioconj. Chem.* (1994) 5(4):333–338
29. Gauthier et al., *Arch Biochem Biophys* (1993) 306:304
30. Geahlen et al., *Anal Biochem* (1992) 202:68
31. Geysen et al., *Proc. Nat. Acad. Sci. U.S.A.* (1984), 81:3998–4002
32. Gordon et al., *J. Med. Chem.* (1994) 37:1385–1401
33. Hermason et al., In: Bioconjigate Techniques, Academic Press, San Diego, Calif., pp 98–100, (1996)
34. Higuchi et al., U.S. Pat. No. 3,710,795
35. Hogan et al., WO 94/01102
36. Hono et al., *Chem. Soc. Jpn.* (1991) 64:111
37. Houghten et al., *Proc. Natl. Acad. Sci. U.S.A.* (1985) 82:5131–35
38. Houghten et al., *Nature* (1991) 354:84–86
39. Hromas et al., *Blood* (1997) 89(9):3315
40. Jiang, et al., *Intl J Peptide Prot. Res* (1995) 45:106
41. Kao et al., "Optical Microscopy: Emerging Methods and Applications," B. Herman, J. J. Lemasters, eds., pp. 27–85 (1993)
42. Kent et al., WO 96/34878
43. Kent et al., WO 98/28434
44. Kravick et al., *Arch. Intern. Med.* (1997) 157:2069–2073
45. Lam et al., *Nature* (1991) 354:82–84
46. Lundblad et al., In: Chemical Reagents for Protein Modification, CRC Press, Boca Raton, Fla., (1984)
47. Lu et al., *J. Am. Chem. Soc.* (1996) 118:8518
48. Lu et al., *Biochemistry* (1997) 36(4): 673
49. Maggiora et al., *J Med Chem* (1992) 35:3727
50. McKnight et al., *Virology* (1994) 201:8–18
51. Moos et al., *Ann. Rep. Med. Chem.* (1993)28:315–324
52. Muir et al., *Curr. Opin. Biochem.* (1993) 4:420
53. Needels et al., *Proc. Natl. Acad. Sci. USA* (1993) 90:10700–10704
54. Neote et al., *Cell* (1993) 72:415–425
55. Nielsen et al., *J Am. Chem. Soc.* (1993) 115:9812–9813
56. Oberlin et al., *Nature* (1996) 382:833
57. Oh et al., *Science* (1996) 273:810–812
58. Oikawa et al., *Cancer* (1991) 59:57–66
59. Oppenheim, *Adv. Exp. Med. Biol.* (1993) 351:183
60. Patchornik et al., *J Am Chem Soc* (1970) 92:6333
61. Pavia et al., *Bioorganic Medicinal Chem. Lett.* (1993) 3:387–96
62. Peled et al., *Biochemistry* (1994) 33:7211
63. "Recombinant Gene Expression Protocols," (1996) Humana Press
64. Risau et al., *Nature* (1997) 387:671–674
65. Rose et al., *J. Amer. Chem. Soc.* (1994) 116:30–33
66. Sambrook et al., (1989) "Molecular Cloning, A Laboratory Manual," Cold Springs Harbor Press, New York
67. Schnolzer et al., *Int. J. Peptide Protein Res.* (1992) 40:180
68. Schnolzer et al., *Science* (1992) 256:221–225
69. Schwartz et al., *Proc. Natl. Acad. Sci. USA* (1997) 56:785–791
70. Siani et al., IBC 3rd Annual International Conference: Chemokines, September 1996
71. Siani et al., NMHCC, Chemokines and Host-Cell Interaction Conference, January 1997, Baltimore, Md.
72. Siani et al., Peptide Symposium, Nashville, June 1997
73. Siani, et al., American Peptide, Jun. 15–19, 1997
74. Simons et al., *J. Virol.* (1996) 70:8355–8360
75. Simons et al., *Science* (1997) 275:1261–1264
76. Simons et al., *Science* (1997) 276:276–279
77. Simons et al., *Cancer* (1998) 82:553–560
78. Smith G. P., *Science* (1985) 228:1315–1317
79. Strahilevitz et al., *Biochemistry* (1994) 33:1
80. Sykes et al., *Science* (1994) 264:90
81. Tam et al., *Proc. Natl. Acad. Sci USA* (1995) 92:12485
82. Tam et al., WO 95/00846
83. Thompson et al., U.S. Provisional Application Ser. No. 06/079,957
84. Trkola et al., *Nature* (1996) 384:184–186
85. Van der Meer et al., (1994) "Resonance Energy Transfer Theory and Data," VCH Publishers
86. Wernette-Hammond et al., *J. Biol. Chem.* (1996) 271:8228–8235

87. Wilken et al., *Curr. Opin. Biotech.* (1998) 9(4):412–426
88. Wu et al., *Analytical Biochem.* (1994) 218:1–13
89. Wu et al., *J. Exp. Med.* (1997) 185:168–169
90. Zhang et al., *Proc. Natl. Acad. Sci. USA* (1998) 95(16):9184–9189
91. Zuckermann et al., *J. Med. Chem* (1994), 37:2678–85

All publications and patent applications mentioned in this specification are herein incorporated by reference to the same extent as of each individual publication or patent application was specifically and individually indicated to be incorporated by reference.

The invention now having been fully described, it will be apparent to one or ordinary skill in the art that many changes and modifications can be made thereto without departing from the spirit or scope of the appended claims.

---

What is claimed is:

1. A method of producing a cross-over chemokine protein that contains at least one peptide segment whose sequence is derived from a first chemokine protein, and at least one peptide segment whose sequence is derived from a second chemokine protein, wherein said second chemokine protein has an amino acid sequence that is different from that of said first chemokine protein, and wherein each of said peptide segments possesses an N-terminal amino acid residue and a C-terminal amino acid residue, said method comprising:

ligating under chemoselective chemical ligation conditions (i) at least one peptide segment comprising a functional protein module derived from said first chemokine protein, and (ii) at least one peptide segment comprising a functional protein module derived from said second chemokine protein, wherein each of said peptide segments exhibit sufficient homology to a functional protein module of a chemokine to permit said peptide segments to mediate the function of the chemokine functional protein module when incorporated into said cross-over chemokine protein, and wherein the C-terminal residue of said peptide segment derived from said first chemokine protein and the N-terminal residue of said peptide segment derived from said second chemokine protein comprise compatible reactive groups capable of chemoselective chemical ligation to one another, whereby a covalent bond is formed between said compatible reactive groups of said peptide segments so as to produce a chemical ligation product comprising a cross-over chemokine protein in which the C-terminal residue of the peptide segment derived from said first chemokine protein is ligated to the N-terminal residue of said peptide segment derived from said second chemokine protein.

2. The method of claim 1 further comprising the step of conducting one or more additional ligations with one or more additional peptide segments, each possessing an N-terminal amino acid residue and a C-terminal amino acid residue, comprise a compatible reactive group capable of chemoselective chemical ligation to said cross-over chemokine protein.

3. The method of claim 1, wherein said chemoselective chemical ligation is selected from the group consisting of native chemical ligation, oxime forming chemical ligation, thioester forming ligation, thioether forming ligation, hydrazone forming ligation, thiazolidine forming ligation, and oxazolidine forming ligation.

4. A method of producing a cross-over chemokine protein library whose members contain two or more peptide segments, wherein each of said peptide segments exhibit sufficient homology to a functional protein module of a chemokine to permit said peptide segments to mediate the function of said functional protein module when incorporated into said cross-over chemokine protein, each segment possessing an N-terminal amino acid residue and a C-terminal amino acid residue, and wherein the peptide segments of said members are derived from two or more different chemokine protein molecules, said method comprising:

incubating under chemoselective ligation reaction conditions a plurality of unique peptide segments each comprising one or more functional protein modules derived from a member of a first set of chemokine protein molecules and a plurality of unique peptide segments each comprising one or more functional protein modules derived from a member of a second set of chemokine protein molecules wherein the C-terminal residues of each of said peptide segments derived from said members of said first set of protein molecules and the N-terminal residue of each of said peptide segments derived from said members of said second set of protein molecules comprise compatible reactive groups capable of chemoselective chemical ligation to one another, whereby a covalent bond is formed between said compatible reactive groups of said peptide segments so as to produce a plurality of chemical ligation products comprising a plurality of unique cross-over chemokine proteins, wherein, for each such cross-over chemokine protein, the C-terminal residue of a peptide segment derived from a member of said first set of chemokine protein molecules is ligated to the N-terminal residue of a peptide segment derived from a member of said second set of chemokine protein molecules.

5. The method of claim 4, wherein said chemoselective chemical ligation is selected from the group consisting of native chemical ligation, oxime forming chemical ligation, thioester forming ligation, thioether forming ligation, hydrazone forming ligation, thiazolidine forming ligation, and oxazolidine forming ligation.

6. The method of claim 2, wherein said chemoselective chemical ligation is selected from the group consisting of native chemical ligation, oxime forming chemical ligation, thioester forming ligation, thioether forming ligation, hydrazone forming ligation, thiazolidine forming ligation, and oxazolidine forming ligation.

7. The method of claim 1, further comprising the step of adding at least one chemical tag.

8. The method of claim 7, wherein said chemical tags are the same or different and are independently selected from the group consisting of synthesis and purification handles, detectable labels, chemical moieties for attachment to a support matrix, and mixtures thereof.

9. The method of claim 7, wherein the chemical tag is selected from the group consisting of metal binding tags, carbohydrate/substrate binding tags, antibodies, antibody fragment tags, isotopic labels, haptens, unnatural amino acids, chromophores, and mixtures thereof.

10. The method of claim 7, further comprising the step of separating the chemical tag from the cross-over chemokine protein.

11. The method of claim 1 wherein the first and second chemokine proteins are derived from different subfamilies of chemokines.

12. The method of claim 1 wherein the first and second chemokine proteins are derived from different species.

13. The method of claim 1 further comprising the step of preparing the first and second chemokine proteins by chemical synthesis, ribosomomally in a cell free system, ribosomally within a cell, or any combination thereof.

14. The method of claim 1 wherein the first chemokine protein is chemically modified to incorporate D-amino acids, other unnatural amino acids, ester backbone bonds to replace the normal amide bond, alkyl backbone bonds to replace the normal amide bond, N-alkyl substituents, C-alkyl substituents, side chain modifications, disulfide bridges, side chain amide linkages, side chain ester linkages, and combinations thereof.

15. The method of claim 1 wherein the second chemokine protein is chemically modified to incorporate D-amino acids, other unnatural amino acids, ester backbone bonds to replace the normal amide bond, alkyl backbone bonds to replace the normal amide bond, N-alkyl substituents, C-alkyl substituents, side chain modifications, disulfide bridges, side chain amide linkages, side chain ester linkages, and combinations thereof.

16. The method of claim 4, further comprising the step of adding at least one chemical tag.

17. The method of claim 16, wherein said chemical tags are the same or different and are independently selected from the group consisting of synthesis and purification handles, detectable labels, chemical moieties for attachment to a support matrix, and mixtures thereof.

18. The method of claim 16, wherein the chemical tag is selected from the group consisting of metal binding tags, carbohydrate/substrate binding tags, antibodies, antibody fragment tags, isotopic labels, haptens, unnatural amino acids, chromophores, and mixtures thereof.

19. The method of claim 16, further comprising the step of separating the chemical tag from the cross-over chemokine protein.

20. The method of claim 4 wherein the first and second chemokine proteins are derived from different subfamilies of chemokines.

21. The method of claim 4 wherein the first and second chemokine proteins are derived from different species.

22. The method of claim 4 further comprising the step of preparing the first and second chemokine proteins by chemical synthesis, ribosomomally in a cell free system, ribosomally within a cell, or any combination thereof.

23. The method of claim 4 wherein the first chemokine protein is chemically modified to incorporate D-amino acids, other unnatural amino acids, ester backbone bonds to replace the normal amide bond, alkyl backbone bonds to replace the normal amide bond, N-alkyl substituents, C-alkyl substituents, side chain modifications, disulfide bridges, side chain amide linkages, side chain ester linkages, and combinations thereof.

24. The method of claim 4 wherein the second chemokine protein is chemically modified to incorporate D-amino acids, other unnatural amino acids, ester backbone bonds to replace the normal amide bond, alkyl backbone bonds to replace the normal amide bond, N-alkyl substituents, C-alkyl substituents, side chain modifications, disulfide bridges, side chain amide linkages, side chain ester linkages, and combinations thereof.

25. A method of producing a cross-over chemokine protein comprising a single ligation site, comprising:

selecting a first peptide segment whose sequence is derived from a first chemokine protein wherein said first peptide segment possesses an N-terminal amino acid residue and a C-terminal amino acid residue and a functional protein module derived from said first chemokine protein, and wherein said first peptide segment exhibits sufficient homology to a functional protein module of a chemokine to permit said first peptide segment to mediate the function of the chemokine functional protein module when incorporated into said cross-over chemokine protein, selecting a second peptide segment whose sequence is derived from a second chemokine protein, wherein said second peptide segment possesses an N-terminal amino acid residue and a C-terminal amino acid residue and a functional protein module derived from said second chemokine protein, and wherein said first peptide segment exhibits sufficient homology to a functional protein module of a chemokine to mediate the function of the chemokine functional protein module when incorporated into said cross-over chemokine protein, and wherein said second chemokine protein has an amino acid sequence that is difference from that of said first chemokine protein, ligating under chemoselective chemical ligation conditions said first peptide segment with said second peptide segment so that the C-terminal residue of said first peptide segment and the N-terminal residue of said second peptide segment undergo chemoselective chemical ligation to one another, whereby a covalent bond is formed between said compatible reactive groups of said first and second peptide segments so as to produce a chemical ligation product comprising a cross-over chemokine protein in which the C-terminal residue of the first peptide segment is ligated to the N-terminal residue of said second peptide segment.

26. The method of claim 25, further comprising the step of adding at least one chemical tag.

27. The method of claim 26, wherein said chemical tags are the same or different and are independently selected from the group consisting of synthesis and purification handles, detectable labels, chemical moieties for attachment to a support matrix, and mixtures thereof.

28. The method of claim 26, wherein the chemical tag is selected from the group consisting of metal binding tags, carbohydrate/substrate binding tags, antibodies, antibody fragment tags, isotopic labels, haptens, unnatural amino acids, chromophores, and mixtures thereof.

29. The method of claim 26, further comprising the step of separating the chemical tag from the cross-over chemokine protein.

30. The method of claim 25 wherein the first and second chemokine protein segments are derived from different subfamilies of chemokines.

31. The method of claim 25 wherein the first and second chemokine protein segments are derived from different species.

32. The method of claim 25 further comprising the step of preparing the first and second chemokine protein segments by chemical synthesis, ribosomomally in a cell free system, ribosomally within a cell, or any combination thereof.

33. The method of claim 25 wherein the first protein segment is chemically modified to incorporate D-amino acids, other unnatural amino acids, ester backbone bonds to replace the normal amide bond, alkyl backbone bonds to replace the normal amide bond, N-alkyl substituents, C-alkyl substituents, side chain modifications, disulfide bridges, side chain amide linkages, side chain ester linkages, and combinations thereof.

34. The method of claim 1 wherein the second protein segment is chemically modified to incorporate D-amino acids, other unnatural amino acids, ester backbone bonds to replace the normal amide bond, alkyl backbone bonds to replace the normal amide bond, N-alkyl substituents, C-alkyl substituents, side chain modifications, disulfide bridges, side chain amide linkages, side chain ester linkages, and combinations thereof.

35. A method of producing a cross-over chemokine protein, said method comprising:

ligating under chemoselective native chemical ligation conditions (i) a first peptide segment comprising an N-terminal cysteine and a functional protein module derived from a first chemokine protein, and (ii) a second peptide segment comprising a C-terminal thioester and a functional protein module derived from a second chemokine protein, wherein said first and second chemokine proteins each have different amino acid sequences, whereby a native peptide bond is formed between said N-terminal cysteine and said C-terminal thioester so as to produce a chemical ligation product comprising said cross-over chemokine protein.

* * * * *